US011492372B2

(12) United States Patent
Trejo et al.

(10) Patent No.: US 11,492,372 B2
(45) Date of Patent: *Nov. 8, 2022

(54) REMOVAL OF LEAKED AFFINITY PURIFICATION LIGAND

(71) Applicant: AMGEN INC., Thousand Oaks, CA (US)

(72) Inventors: Samuel Ray Trejo, Boxborough, MA (US); Robert Perry Brake, Barrington, RI (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/554,865

(22) Filed: Dec. 17, 2021

(65) Prior Publication Data

US 2022/0144886 A1 May 12, 2022

Related U.S. Application Data

(63) Continuation of application No. 17/517,190, filed on Nov. 2, 2021, which is a continuation of application No. 16/042,965, filed on Jul. 23, 2018, now Pat. No. 11,192,919, which is a continuation of application No. 14/775,992, filed as application No. PCT/US2014/023682 on Mar. 11, 2014, now abandoned.

(60) Provisional application No. 61/785,038, filed on Mar. 14, 2013.

(51) Int. Cl.
| | |
|---|---|
| *B01D 15/36* | (2006.01) |
| *B01D 15/38* | (2006.01) |
| *C07K 1/18* | (2006.01) |
| *C07K 16/00* | (2006.01) |
| *C07K 1/22* | (2006.01) |
| *C07K 14/705* | (2006.01) |
| *C07K 14/715* | (2006.01) |
| *B01D 15/18* | (2006.01) |

(52) U.S. Cl.
CPC ............ *C07K 1/18* (2013.01); *B01D 15/363* (2013.01); *B01D 15/3809* (2013.01); *C07K 14/70575* (2013.01); *C07K 14/7151* (2013.01); *C07K 16/00* (2013.01); *B01D 15/1871* (2013.01); *C07K 1/22* (2013.01); *C07K 2319/30* (2013.01)

(58) Field of Classification Search
None
See application file for complete search history.

(56) References Cited

U.S. PATENT DOCUMENTS

| | | |
|---|---|---|
| 4,695,623 A | 9/1987 | Stabinsky |
| 4,897,471 A | 1/1990 | Stabinsky |
| 4,968,607 A | 11/1990 | Dower et al. |
| 5,075,222 A | 12/1991 | Hannum et al. |
| 5,149,792 A | 9/1992 | Thomason |
| 5,272,064 A | 12/1993 | Thomason |
| 5,395,760 A | 3/1995 | Smith et al. |
| 5,610,279 A | 3/1997 | Brockhaus et al. |
| 5,647,987 A | 7/1997 | Muller et al. |
| 5,767,064 A | 6/1998 | Sims et al. |
| 5,856,296 A | 1/1999 | Mosley et al. |
| 5,866,673 A | 2/1999 | Muller et al. |
| 5,981,713 A | 11/1999 | Colotta et al. |
| 6,015,938 A | 1/2000 | Boyle et al. |
| 6,096,728 A | 8/2000 | Collins et al. |
| 6,149,994 A | 11/2000 | Muller et al. |
| 6,204,363 B1 | 3/2001 | Zsebo et al. |
| 6,235,883 B1 | 5/2001 | Jakobovits et al. |
| 6,271,349 B1 | 8/2001 | Dougall et al. |
| 6,398,962 B1 | 6/2002 | Cabrera et al. |
| 6,337,072 B1 | 8/2002 | Ford et al. |
| 7,186,410 B2 | 3/2007 | Chtourou et al. |
| 7,476,722 B2 | 1/2009 | Vedantham et al. |
| 8,067,182 B2 | 11/2011 | Kelley et al. |
| 11,192,919 B2* | 12/2021 | Trejo ................ C07K 14/7151 |
| 2013/0195849 A1* | 8/2013 | Spreter Von Kreudenstein ......... C07K 16/46 530/387.3 |
| 2013/0245139 A1 | 9/2013 | Kozlov et al. |
| 2014/0187751 A1 | 7/2014 | Nti-Gyabaah et al. |

FOREIGN PATENT DOCUMENTS

| | | |
|---|---|---|
| AU | 588819 A | 3/1998 |
| EP | 0 367 566 B1 | 5/1990 |
| EP | 0 460 846 A1 | 12/1991 |
| EP | 0337144 B1 | 5/1992 |
| EP | 2969099 B1 | 1/2016 |
| JP | 2005538686 | 12/2005 |
| JP | 2010209068 | 9/2010 |

(Continued)

OTHER PUBLICATIONS

Aggarwal and Gutterman, eds., Human Cytokines: Handbook for Basic and Clinical Research, Blackwell Sciences, Cambridge, MA, 1998.
CAS registry No. 185243-69-0. Retrieved from http://www.commonchemistry.org/ChemicalDetail.aspx?ref=185243-69-0, Jan. 24, 2018.
Corbett, Rachel, et al., "Structure and protein adsorption mechanisms of clean and fouled tentacle-type anion exchangers used in a monoclonal antibody polishing step", Journal of Chromatography A, vol. 1278, Feb. 1, 2013, pp. 116-125.
Devereux, et al., "A comprehensive set of sequence analysis programs for the VAX" *Nucleic Acids Res.* Jan. 11, 1984;12(1 Pt 1):387-95.

(Continued)

*Primary Examiner* — Daniel E Kolker
*Assistant Examiner* — James L Rogers

(57) ABSTRACT

The invention provides for the removal of a large fraction of contaminants from protein preparations while maintaining a high level of recovery using tentacle anion exchange matrix chromatography medium. Using the methods of the invention, leached affinity chromatography contaminants can be removed from recombinant protein preparations.

28 Claims, 2 Drawing Sheets

(56) References Cited

FOREIGN PATENT DOCUMENTS

| WO | 94/10308 A1 | 5/1994 |
|---|---|---|
| WO | 94/28391 A1 | 12/1994 |
| WO | 97/01633 A1 | 1/1997 |
| WO | 01/36637 A1 | 5/2001 |
| WO | 2003/059935 A2 | 7/2003 |
| WO | 06/099308 A2 | 9/2006 |
| WO | 2012/176158 A1 | 12/2012 |
| WO | 2013/009526 A1 | 1/2013 |

OTHER PUBLICATIONS

Do and Chen-Kiang, "Mechanism of BLyS action in B cell immunity." Cytokine Growth Factor Rev. Feb. 2002;13(1):19-25.
Ford et al., "Affinity purification of novel bispecific antibodies recognising carcinoembryonic antigen and doxorubicin"; *J Chromatogr B Biomed Sci Appl*. Apr. 25, 2001;754(2):427-35.
Gribskov and Burgess, "Sigma factors from *E. coli*, B. subtilis, phage SP01, and phage T4 are homologous proteins." *Nucleic Acids Res*. Aug. 26, 1986;14(16):6745-63.
Håkansson, et al., "Crystal structure of the trimeric α-helical coiled-coil and the three lectin domains of human lung surfactant protein D." *Structure*. Mar. 15, 1999;7(3):255-64.
Han et el., "Chapter 14: Recovery and Purification of Antibody," Jan. 1, 2011, Cell Engineering 7: Antibody Expression and Produc, Springer Science & Business Media, pp. 305-340, XP009178601.
Harbury, et al., "A switch between two-, three-, and four-stranded coiled coils in GCN4 leucine zipper mutants." *Science*. Nov. 26, 1993; 262:1401-7.
Harbury, et al., "Crystal structure of an isoleucine-zipper trimer." *Nature*. Sep. 1, 1994;371:80-3.
International Preliminary Report on Patentability for PCT/US2014/023682 dated Sep. 15, 2015.
International Search Report for PCT/US2014/023682 dated Jun. 27, 2014.
Iskra, Timothy et al., "The effect of protein a cycle number on the performance and lifetime of an anion exchange polishing step", Biotechnology and Bioengineering, vol. 110, No. 4, Apr. 2013, pp. 1142-1152.
Lovejoy, et al., "Crystal structure of a synthetic triple-stranded alpha-helical bundle." *Science*. Feb. 26, 1993; 259(5099):1288-93.
Kelley, Brian D., et al. "High-throughput screening of chromatographic separations: IV. Ion-exchange", Biotechnology and Bioengineering, vol. 100, No. 5, Aug. 1, 2008, pp. 950-963.
Maisonpierre, et al., "Angiopoietin-2, a natural antagonist for Tie2 that disrupts in vivo angiogenesis." *Science*. Jul. 4, 1997; 277(5322):55-60.
McKay and Leigh, "Growth Factors: A Practical Approach", 1993.
Merk: "MERCK: Fractogel (R) EMD chromatography for pharmaceutics manufacturing", Wenku.baidu.com, Aug. 5, 2010.
Ostrove, "Guide to Protein Purification, Methods Enzymol". 1990; 182:357-79.
Reen, "Enzyme-Linked Immunosorbent Assay (ELISA), in Basic Protein and Peptide Protocols, Methods Mol. Biol.", 1994; 32: 461-466.
Remington's Pharmaceutical Sciences, 18th ed. 1990.
Rüegg and Pytela, "Sequence of a human transcript expressed in T-lymphocytes and encoding a fibrinogen-like protein," *Gene*. Jul. 28, 1995; 160(2):257-62.
Schwartz and Dayhoff, "Atlas of Protein Sequence and Structure", *National Biomedical Research Foundation*, 1978; 353-358.
Susumu Sekine, 'Koutai Iyakuno Genjou To Kadai' ('Current status and tasks of Antibody drugs' in Japanese), Science & Technology Trends, Oct. 2009, pp. 13-25 [English translation only].
Stoschek, "Quantitation of Protein in Guide to Protein Purification"; 182: 50-68.
Tugcu, et al., "Maximizing productivity of chromatography steps for purification of monoclonal antibodies." *Biotechnol Bioeng*. Feb. 15, 2008;99(3):599-613.
Vola, et al. "Recombinant proteins L and LG. Two new tools for purification of murine antibody fragments." *Cell Biophys*. 1994;24-25:27-36.
Yamato Yoshikawa et al., 'Section 5. Ion Exchange Chromatography' in 'Tanpakushitsu Jikkenn Note' ('Lab Notes for Protein Experiment' in Japanese) vol. 1, 'Muteki No BioTechnical Series' ('Invincible BioTechnical Series' in Japanese), published by Yodosha, Oct. 15, 1998, the 5th impression, pp. 107-114 [English translation only].
Written Opinion for PCT/US2014/023682 dated Jun. 27, 2014.
Datenblatt Eshmuno Q, EMD Millipore Corporation, Feb. 2017.
Page 16 of EP2969099.
Pages 20-25 of EP2969099.
Shukla et al., "Process Scale Bioseparations For the Biopharmaceutical Industry", Taylor & Francis Group, LLC 2007, Chapter 6.
Shukla et al., "Process Scale Bioseparations For the Biopharmaceutical Industry", Taylor & Francis Group, LLC 2007, Chapter 17.
Notice of Opposition dated Jan. 25, 2019, Opposition against European Patent 2969099.
Acknowledgement of Receipt for EP Application 14714890.2 dated Jun. 17, 2019.
Annex to Expert Declaration of Robert P. Brake.
Auxiliary Request 1 (clean version) for EP Application 14714890.2 dated Jun. 17, 2019.
Auxiliary Request 1 (marked version) for EP Application 14714890.2 dated Jun. 17, 2019.
Auxiliary Request 1 (marked version) for EP Application 14714890.2 dated Apr. 1, 2020.
Auxiliary Request 1 (clean version) for EP Application 14714890.2 dated Apr. 1, 2020.
Auxiliary Request 2 (clean version) for EP Application 14714890.2 dated Jun. 17, 2019.
Auxiliary Request 2 (marked version) for EP Application 14714890.2 dated Jun. 17, 2019.
Auxiliary Request 2 (marked version) for EP Application 14714890.2 dated Apr. 1, 2020.
Auxiliary Request 2 (clean version) for EP Application 14714890.2 dated Apr. 1, 2020.
Auxiliary Request 3 (clean version) for EP Application 14714890.2 dated Jun. 17, 2019.
Auxiliary Request 3 (marked version) for EP Application 14714890.2 dated Jun. 17, 2019.
Auxiliary Request 3 (marked version) for EP Application 14714890.2 dated Apr. 1, 2020.
Auxiliary Request 3 (clean version) for EP Application 14714890.2 dated Apr. 1, 2020.
Auxiliary Request 4 (clean version) for EP Application 14714890.2 dated Apr. 1, 2020.
Auxiliary Request 4 (marked version) for EP Application 14714890.2 dated Apr. 1, 2020.
Auxiliary Request 5 (marked version) for EP Application 14714890.2 dated Apr. 1, 2020.
Auxiliary Request 5 (clean version) for EP Application 14714890.2 dated Apr. 1, 2020.
Auxiliary Request 6 (marked version) for EP Application 14714890.2 dated Apr. 1, 2020.
Auxiliary Request 6 (clean version) for EP Application 14714890.2 dated Apr. 1, 2020.
Auxiliary Request 7 (marked version) for EP Application 14714890.2 dated Apr. 1, 2020.
Auxiliary Request 7 (clean version) for EP Application 14714890.2 dated Apr. 1, 2020.
Auxiliary Request 7 (marked version) for EP Application 14714890.2 dated Feb. 9, 2021.
Auxiliary Request 7 (clean version) for EP Application 14714890.2 dated Feb. 9, 2021.
Auxiliary Request 8 (marked version) for EP Application 14714890.2 dated Apr. 1, 2020.
Auxiliary Request 8 (clean version) for EP Application 14714890.2 dated Apr. 1, 2020.
Auxiliary Request 9 (marked version) for EP Application 14714890.2 dated Apr. 1, 2020.

(56) References Cited

OTHER PUBLICATIONS

Auxiliary Request 9 (clean version) for EP Application 14714890.2 dated Apr. 1, 2020.
Auxiliary Request 10 (marked version) for EP Application 14714890.2 dated Feb. 9, 2021.
Auxiliary Request 10 (clean version) for EP Application 14714890.2 dated Feb. 9, 2021.
Auxiliary Request 11 (marked version) for EP Application 14714890.2 dated Feb. 9, 2021.
Auxiliary Request 11 (clean version) for EP Application 14714890.2 dated Feb. 9, 2021.
Auxiliary Request 12 (marked version) for EP Application 14714890.2 dated Feb. 9, 2021.
Auxiliary Request 12 (clean version) for EP Application 14714890.2 dated Feb. 9, 2021.
Auxiliary Request 13 (marked version) for EP Application 14714890.2 dated Feb. 9, 2021.
Auxiliary Request 13 (clean version) for EP Application 14714890.2 dated Feb. 9, 2021.
Brief Communication in Opposition Proceedings with letter from the opponent 01 of Jul. 5, 2020 for EP Application 14714890.2 dated May 13, 2020.
Brief Communication in Opposition Proceedings with letter from the opponent 01 of Jul. 5, 2020 for EP Application 14714890.2 dated Feb. 18, 2021.
Expert Declaration of Robert P. Brake.
Fractogel EDM Merck Process Media.
Fractogel EDM Merck IEX Chrom Media.
Fractogel EMD Tentacles Resins Technical Seminar.
Interlocutory decision in Opposition proceedings (Art. 101(3)(a) and 106(2) EPC) dated May 3, 2021, reasons for the decision, and meeting minutes of oral proceedings.
Main Request (claims as granted) for EP Application 14714890.2 dated Jun. 17, 2019.
Proprietors Observations in Response to the Communication of Notices of Opposition Pursuant to Rule 79(1) EPC for EP Application 14714890.2 dated Jun. 17, 2019.
Proprietor's Submission in Response to the Summons to Attend Oral Proceedings pursuant to Rule 115(1) EPC dated Aug. 16, 2019 and Auxiliary Requests 1-9, Apr. 1, 2020.
Proprietor's Submission in Response to Opponent's Submission dated May 7, 2020 and Auxiliary Requests 1-13, Feb. 9, 2021.
Submission in Opposition Proceedings for EP Application 14714890.2 dated Jun. 17, 2019.
Summons to attend oral proceedings pursuant to Rule 115(1) EPC for EP Application 14714890.2 dated Aug. 16, 2019.
Summons to attend oral proceedings pursuant to Rule 115(1) EPC for EP Application 14714890.2 dated Jul. 8, 2020.
Table pertaining to Example 8 (EP 2 696 099 B1).
Vijayalashim, MA, Biochromatography Theory and Practice, Taylor & Francis Publishing, Nov. 3, 2006.

\* cited by examiner

REMOVAL OF LEAKED AFFINITY PURIFICATION LIGAND

CROSS-REFERENCE TO RELATED APPLICATIONS

This application is a continuation application of U.S. application Ser. No. 17/517,190, filed Nov. 2, 2021, which is a continuation of U.S. application Ser. No. 16/042,965, filed Jul. 23, 2018, which is a continuation application U.S. application Ser. No. 14/775,992, filed Sep. 14, 2015, which is a 371 of PCT/US2014/023682, filed Mar. 11, 2014, which claims priority to the benefit of U.S. Provisional Application No. 61/785,038, filed Mar. 14, 2013. The above-identified applications are each hereby incorporated herein by reference for all purposes.

FIELD OF THE INVENTION

The invention is in the field of removal of contaminants from protein preparations. In one aspect, the invention relates to the removal of leached affinity chromatography contaminants from a protein preparation.

BACKGROUND OF THE INVENTION

Affinity chromatography is a powerful tool for purification of proteins such as antibodies and Fc-fusion proteins. However, if the proteins are manufactured for therapeutic use, the presence of other proteins, including a protein used as part of an affinity adsorbent, which can leach into a sample during affinity chromatography, is of concern. In addition, other protein contaminants may also be present in a sample, such as, for example, proteins derived from host cells that produce the protein being purified.

Proteins A and G are often employed to purify antibodies by affinity chromatography. Ford et al. (2001), J. Chromatogr. B 754: 427-435. These proteins are useful because they bind to a constant (Fc) portion of many different antibodies. Recombinant fusion proteins including an Fc portion of an IgG antibody can be purified using similar methods. In most protein A and protein G affinity chromatography operations, small amounts of the protein A or G ligand leach from the affinity column and end up in the eluate as either free ligand or ligand in complex with the target protein. If the antibody or fusion protein will be used as a therapeutic, the leached ligand and ligand/protein complexes must be removed.

Manufacturers of chromatography resins recommend using ion exchange chromatography to remove residual contaminants such as protein A. See, e.g., "Process Scale Antibody Purification" Application Note 11-0011-64 AA, 2004-11 (GE Healthcare). Kelley et al. reported that cation exchange chromatography is more typically used in a bind and elute mode, where impurities less basic than the product are removed in the load and wash, and more basic impurities are separated from the product during elution. Kelley et al., 2008, Biotechnol. and Bioeng., vol. 100: 950-963. According to the same authors, anion exchange chromatography is usually operated in a flow through mode, since polyanions such as endotoxin and nucleic acids can be bound to the column under conditions that allow the desired product to flow through. Id. at 950. Anion exchange chromatography in a flow through mode can also typically be used to remove host cell proteins and protein A. Id. at 961.

Hydroxyapatite chromatography is surprisingly effective at removing leached protein A during process scale protein production. U.S. Pat. No. 7,476,722 describes that a hydroxyapatite column can be operated in flow through mode while maintaining over 90% recovery of the target protein and reduction in contaminating Protein A of from 5.3 to 5.4 fold. However, in some situations, hydroxyapatite may not be convenient to use because of mechanical instability and/or low reusability, or may not sufficiently remove all of the leached protein A. Thus, there is a need in the art for alternative ways of removing leached protein A, while at the same time maximizing recovery of protein and thereby controlling the costs of recombinant protein production.

SUMMARY OF THE INVENTION

Although affinity chromatography is a highly effective technique for isolating proteins, one drawback is that the affinity ligand may contaminate the resulting sample of recombinant protein by leaching from the affinity chromatography medium. Because affinity ligands are chosen for their ability to associate with the recombinant protein, it can be challenging to remove them from a final preparation without also losing the recombinant protein. The invention provides an effective, gentle, and easily scalable way of accomplishing this goal using tentacle anion exchange matrix chromatography medium. While not wishing to be bound to any particular mechanism, it is thought that the tentacle aspect of the anion exchange matrix chromatography medium gives the methods of the invention unexpectedly better results than that observed with any other type of anion exchange resin, or indeed most resins, in removing affinity ligand without significant losses in recovery of the recombinant protein.

Accordingly, the method provides, in one aspect, a method for purifying a recombinant protein from a sample containing the recombinant protein and a second protein that binds to the protein, comprising subjecting the sample to a tentacle anion exchange matrix chromatography medium under conditions whereby the recombinant protein binds to the tentacle anion exchange matrix chromatography medium, followed by eluting the recombinant protein bound to the chromatography medium in an eluant, whereby at least 85% of the recombinant protein is recovered in the eluant and at least 75% of the second protein is removed from the eluant. In one aspect, the tentacle anion exchange matrix chromatography medium contains a strong anion functional group. Such a strong anion functional group can be trimethyl-ammoniumethyl (TMAE). The resin substrate of the tentacle anion exchange matrix chromatography medium can be a methacrylate polymeric resin or a polyvinylstyrene polymeric resin. In one aspect of the above embodiments, the chromatography medium is Fractogel® EMD TMAE HiCap.

In all of the above embodiments, the methods of the invention can be used to purify recombinant protein containing a $C_H2/C_H3$ region of an antibody. Such proteins can be purified on affinity columns such as a Protein A or Protein G chromatography resin. Accordingly, the methods of the invention can be used when the second protein is Protein A or Protein G. In any one of the above embodiments, the sample can be obtained from affinity purification of the protein. Such an affinity purification can be over a Protein A chromatography medium.

In any of the above aspects of the invention, the recombinant protein can be an antibody or an Fc fusion protein. In one embodiment of the above aspects, the recombinant protein is a tumor necrosis factor receptor Fc fusion protein, such as, for example, etanercept.

Optionally, in any of the above aspects of the invention, after the recombinant protein is bound to the tentacle anion exchange matrix chromatography medium and before the recombinant protein is eluted, the tentacle anion exchange matrix chromatography medium can subjected to a wash step. As another option in any of the above aspects of the invention, the recombinant protein can be subjected to further purification before and/or after the tentacle anion exchange matrix chromatography. Such additional purification steps include but are not limited to affinity chromatography, ion exchange chromatography, hydroxyapatite chromatography, hydrophobic interaction chromatography, a gel filtration (size exclusion) chromatography, mixed mode chromatography, and/or filtration. In addition, in all of the above aspects of the invention, the recombinant protein can also be subsequently formulated into a pharmaceutical composition.

DETAILED DESCRIPTION

Definitions

Figure 1:
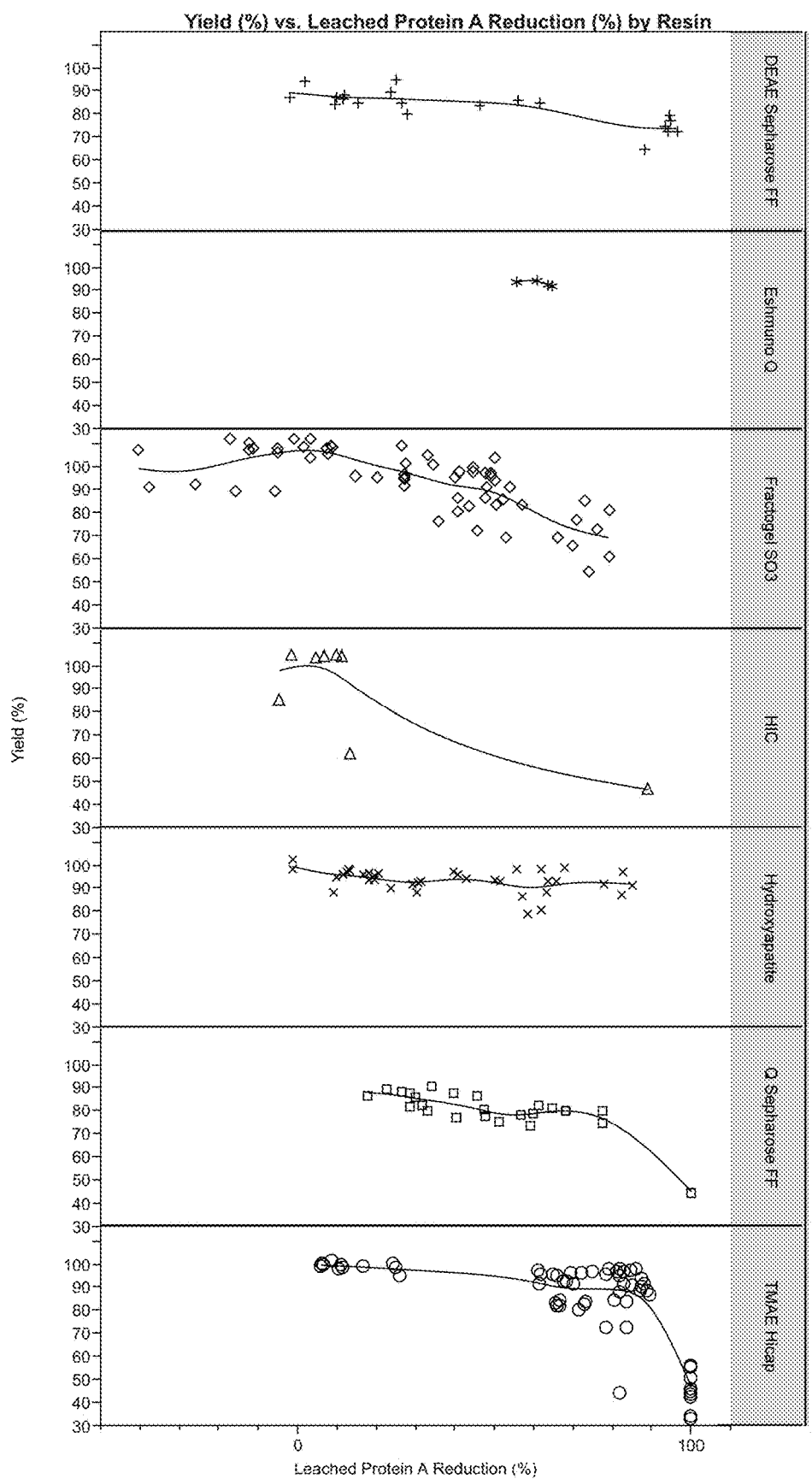
FIG. 1 shows the compiled results of screening and optimization experiments for each of the indicated resins as taken from working examples 1 through 8. The recovery of the test recombinant protein, etanercept, is graphed on the Y-axis as a function of percent leached protein A reduction, which is plotted on the X-axis. Resins used are indicated and were as follows: DEAE Sepharose Fast Flow (GE Healthcare Life Sciences); Eshmuno® Q (EMD Millipore); Fractogel® SO3 (Merck Millipore); HIC (Toyopearl 650-M; ToyoScreen Ether-650M; ToyoScreen Phenyl-650M; ToyoScreen PPG-600M, all from Tosoh Bioscience GmbH); CHT Ceramic Hydroxyapatite Type II 80 µm particle resin (Bio-Rad Laboratories, Inc., Hercules, Calif.); Q Sepharose Fast Flow (GE Healthcare Life Sciences); and Fractogel® EMD TMAE HiCap (EMD Millipore).

Adsorbent: An adsorbent is at least one molecule affixed to a solid support or at least one molecule that is, itself, a solid, which is used to perform chromatography.

Affinity chromatography: Affinity chromatography is chromatography that utilizes the specific, reversible interactions between biomolecules, for example, the ability of Protein A to bind to an Fc portion of an IgG antibody, rather than the general properties of a molecule, such as isoelectric point, hydrophobicity, or size, to effect chromatographic separation. In practice, affinity chromatography involves using an adsorbent, such as Protein A affixed to a solid support, to chromatographically separate molecules that bind more or less tightly to the adsorbent. See Ostrove (1990) in *Guide to Protein Purification*, Methods in Enzymology 182: 357-379, which is incorporated herein in its entirety.

Chromatography: Chromatography is the separation of chemically different molecules in a mixture from one another by percolation of the mixture through an adsorbent, which adsorbs or retains different molecules more or less strongly. Molecules that are least strongly adsorbed to or retained by the adsorbent are released from the adsorbent under conditions where those more strongly adsorbed or retained are not.

Contaminant: A contaminant is any foreign or objectionable molecule, particularly a biological macromolecule such as a DNA, an RNA, or a protein, other than the protein being purified that is present in a sample of a protein being purified. Contaminants include, for example, other proteins from cells that secrete the protein being purified and proteins, such as Protein A, that are part of an adsorbent used for affinity chromatography that may leach into a sample during affinity chromatography.

Purify: To purify a protein means to reduce the amounts of foreign or objectionable elements, especially biological macromolecules such as proteins or DNA that may be present in a sample of the protein. The presence of foreign proteins may be assayed by any appropriate method including gel electrophoresis and staining and/or ELISA assay. The presence of DNA may be assayed by any appropriate method including gel electrophoresis and staining and/or assays employing polymerase chain reaction.

Separate: A protein is separated from a second protein in a mixture comprising both proteins when the mixture is subjected to a process such that at least the majority of the molecules of the protein are removed from that portion of the mixture that comprises at least the majority of the molecules of the second protein.

Substantially similar: For purposes of the invention, proteins are substantially similar if they are at least 80%, preferably at least 90% identical to each other in amino acid sequence and maintain or alter in a desirable manner the biological activity of the unaltered protein. Included in amino acids considered identical for the purpose of determining whether proteins are substantially similar are amino acids that are conservative substitutions, unlikely to affect biological activity, including the following: Ala for Ser, Val for Ile, Asp for Glu, Thr for Ser, Ala for Gly, Ala for Thr, Ser for Asn, Ala for Val, Ser for Gly, Tyr for Phe, Ala for Pro, Lys for Arg, Asp for Asn, Leu for Ile, Leu for Val, Ala for Glu, Asp for Gly, and these changes in the reverse. See e.g. Neurath et al., *The Proteins*, Academic Press, New York (1979). The percent identity of two amino sequences can be determined by visual inspection and mathematical calculation, or more preferably, the comparison is done by comparing sequence information using a computer program such as the Genetics Computer Group (GCG; Madison, Wis.) Wisconsin package version 10.0 program, 'GAP' (Devereux et al., 1984, *Nucl. Acids Res.* 12: 387) or other comparable computer programs. The preferred default parameters for the 'GAP' program includes: (1) the weighted amino acid comparison matrix of Gribskov and Burgess ((1986), *Nucl. Acids Res.* 14: 6745), as described by Schwartz and Dayhoff, eds., *Atlas of Polypeptide Sequence and Structure*, National Biomedical Research Foundation, pp. 353-358 (1979), or other comparable comparison matrices; (2) a penalty of 30 for each gap and an additional penalty of 1 for each symbol in each gap for amino acid sequences; (3) no penalty for end gaps; and (4) no maximum penalty for long gaps. Other programs used by those skilled in the art of sequence comparison can also be used.

DESCRIPTION OF THE METHODS OF THE INVENTION

The invention provides a method of purifying a recombinant protein from a sample containing a second protein that binds to the protein. The method entails subjecting the sample to a tentacle anion exchange matrix chromatography medium under conditions whereby the recombinant protein binds to the tentacle anion exchange matrix chromatography medium, followed by eluting the recombinant protein bound to the chromatography medium in an eluant. Using the methods of the invention, the present inventors were able to recover at least 85% of the recombinant protein in the eluant while removing at least 75% of the second contaminating protein. Indeed, the methods of the invention were such that in many conditions, one can recover at least 90% of the recombinant protein in the eluant while at the same time removing at least 80% of the second contaminating protein. Such superior results were not possible with any other anion, cation, or hydrophobic interaction chromatography typically used in industrial production. While not wishing to be bound to any particular mechanism, it is thought that the tentacle aspect of the anion exchange matrix chromatography medium gives the methods of the invention unexpectedly better results than that observed with any other type of anion exchange resin, or indeed most resins.

The term "tentacle anion exchange matrix chromatography medium" refers to an anion exchange matrix implementing tentacle technology typically as disclosed in U.S. Pat. Nos. 6,398,962, 6,149,994, 5,866,673, or 5,647,987. Anion exchange matrices implementing the tentacle technology are resin particles comprising, usually on their surface, spacers formed by linear polymer chains (tentacles), wherein functional groups having anion exchange activity are attached to the tentacles. In a further embodiment, the polymer chains forming said tentacles are acrylamide polymers. In some embodiments, the functional group is selected from the group consisting of TMAE (Trimethylaminoethyl-), DMAE (Dimethylaminoethyl-), and DEAE (Diethylaminoethyl-). In some embodiments, the functional group is a strong anion exchanger. In a particular embodiment, the strong anion exchanger functional group is TMAE.

In one aspect, the resin substrate of the tentacle anion exchange matrix chromatography medium is a methacrylate polymeric resin or a polyvinylstyrene polymeric resin. In one embodiment, the methacrylate or polyvinylstyrene polymer is crosslinked. In the examples described herein, the resin particles consist of crosslinked methacrylate polymer. Examples of tentacle anion exchange matrices are Fractogel® EMD TMAE, Fractogel® EMD TMAE HiCap, Fractogel® EMD TMAE MedCap(m), and Fractoprep® DEAE ion exchangers (EMD Millipore).

In one aspect, the tentacle anion exchange matrix chromatography medium comprises (i) resin particles of methacrylate polymer or of vinyl polymer, such as methacrylate polymer, that can be cross-linked methacrylate polymer, (ii) acrylamide tentacles, wherein the acrylamide tentacles are attached to the surface of said resin particles, and wherein TMAE (Trimethylaminoethyl-) groups are attached to the acrylamide tentaclesfunctional.

The methods of the invention are particularly useful for when the second protein is a leached protein from an affinity chromatography medium over which the recombinant protein has been previously initially purified. Thus, in one embodiment, the sample containing the recombinant protein and the second protein is obtained as a result of a prior affinity chromatography step. The most common affinity chromatography proteins currently in use are Protein A, Protein G, and Protein LG, which are used to bind antibodies or other proteins that contain a $C_H2/C_H3$ region of an antibody such as Fc fusion proteins. However, the second protein can be any other protein that binds to the recombinant protein depending upon the structure of the recombinant protein.

Protein A is a protein originally discovered in the cell wall of *Stapphylococcus* that binds specifically to an Fc portion of an IgG antibody. For purposes of the invention, "Protein A" is any protein identical or substantially similar to *Staphylococcal* Protein A, including commercially available and/or recombinant forms of Protein A. For purposes of the invention, the biological activity of Protein A for the purpose of determining substantial similarity is the capacity to bind to an Fc portion of IgG antibody.

Protein G is a protein originally discovered in the cell wall of Streptococcus that binds specifically to an Fc portion of an IgG antibody. For purposes of the invention, "Protein G" is any protein identical or substantially similar to Streptococcal Protein G, including commercially available and/or recombinant forms of Protein G. For purposes of the invention, the biological activity of Protein G for the purpose of determining substantial similarity is the capacity to bind to an Fc portion of an IgG antibody.

Protein LG is a recombinant fusion protein that binds to IgG antibodies comprising portions of both Protein G (see definition above) and Protein L. Protein L was originally isolated from the cell wall of Peptostreptococcus. Protein LG comprises IgG binding domains from both Protein L and G. Vola et al. (1994) Cell. Biophys. 24-25: 27-36, which is incorporated herein in its entirety. For purposes of the invention, "Protein LG" is any protein identical or substantially similar to Protein LG, including commercially available and/or recombinant forms of Protein LG. For purposes of the invention, the biological activity of Protein LG for the purpose of determining substantial similarity is the capacity to bind to an IgG antibody.

There are many commercially available protein A chromatography media that may be used for affinity purification, including ProSep® controlled-pore glass resins produced by Millipore, and MabSelect™ cross-linked agarose resin products produced by GE Healthcare, formerly Amersham Biosciences. Both Mab Select and ProSep resins have dynamic binding capacities approaching greater than 20 g/L, linear flow velocities for producing commercial quantities of antibodies ranging from 200 to 600 cm/hr, and pH stabilities from about 2 to about 10. Both types of resin are chemically stable when exposed to urea and other reducing agents. A type of protein A chromatography medium that is used in the examples illustrating the invention herein is Mab Select SuRe™ Protein A resin. Mab Select SuRe™ Protein A resin uses an altered recombinant form of protein A which has been genetically engineered to be more stable than native protein A. Leached amounts of protein A derived from a Mab Select SuRe™ Protein A column can also be removed using the methods of the invention. Still another commercially available Protein A chromatography medium is Protein A Sepharose FF resin (GE Healthcare Life Sciences). An example of a commercially available protein G chromatography medium is Protein G Sepharose 4 Fast Flow (GE Healthcare Life Sciences). The methods of the invention entail using known and yet to be developed affinity resins.

The process of the invention can, in some embodiments, also involve at least two steps. First, the recombinant protein undergoes a pre-purification step of affinity chromatography using the second protein affixed to a solid support as an adsorbent. Second, tentacle anion exchange matrix chromatography medium is performed under conditions such that the recombinant protein is bound to the tentacle anion exchange matrix chromatography medium. After an optional wash step, the recombinant protein is eluted from the tentacle anion exchange matrix chromatography medium. The entire process of purifying the protein may include other steps before and/or after each of these steps, as noted below.

Prior to equilibration and chromatography, the tentacle anion exchange matrix chromatography medium may be pre-equilibrated in a chosen solution, e.g. a salt and/or buffer solution. Pre-equilibration serves the function of displacing a solution used for regenerating and/or storing the chromatography medium. One of skill in the art will realize that the composition of the pre-equilibration solution depends on the composition of the storage solution and the solution to be used for the subsequent chromatography. Thus, appropriate pre-equilibration solutions may include the same buffer or salt used for performing the chromatography, optionally, at a higher concentration than is used to perform chromatography. Buffers and salts that can be used for chromatography are discussed below.

Before the sample is applied to the column, the tentacle anion exchange matrix chromatography medium can be equilibrated in the buffer or salt that will be used to chromatograph the protein. As discussed below, chromatography (and loading of the protein to be purified) can occur in a variety of buffers or salts including sodium, potassium, ammonium, magnesium, calcium, chloride, fluoride, acetate, phosphate, and/or citrate salts and/or Tris, phosphate, citrate, HEPES, MOPS, and IVIES buffers. Such buffers or salts can have a pH of at least about 5.5. In some embodiments, equilibration may take place in a solution comprising a Tris or a sodium phosphate buffer. Optionally, the Tris or sodium phosphate buffer is at a concentration between about 0.5 millimolar and about 50 millimolar, more preferably at a concentration between about 15 millimolar and 35 millimolar. Preferably, equilibration takes place at a pH of at least about 5.5. Equilibration may take place at pH values between about 6.0 and about 8.6, preferably at pH values between about 7.0 and 8.5. In one aspect, the solution comprises a Tris buffer at a concentration of about 25 millimolar and at a pH of about 8.

Any or all chromatographic steps of the invention can be carried out by any mechanical means. Chromatography may be carried out in a column. The column may be run with or without pressure and from top to bottom or bottom to top. The direction of the flow of fluid in the column may be reversed during the chromatography process. Chromatography may also be carried out using a batch process in which the solid support is separated from the liquid used to load, wash, and elute the sample by any suitable means, including gravity, centrifugation, or filtration. Chromatography may also be carried out by contacting the sample with a filter that adsorbs or retains some molecules in the sample more strongly than others.

Conditions for binding the recombinant protein to the tentacle anion exchange matrix chromatography medium can be determined by one of skill in the art and are dependent upon the charge of the recombinant protein and the strength of the anion functional group. Optionally, after the recombinant protein is bound to the tentacle anion exchange matrix chromatography medium and before the recombinant protein is eluted, the tentacle anion exchange matrix chromatography medium can be subjected to a wash step. The wash buffer is typically the same buffer system in which the sample has been prepared and subjected to the tentacle anion exchange matrix chromatography medium, although one of skill in the art will be able to determine other buffer conditions for washing the chromatography resin without eluting the recombinant protein. If a wash step is included, the volume of the wash can be small or can be several column volumes. However, typically, the column is washed with from 0.5 to 10 column volumes, more typically from 1 to 5 column volumes. After binding of the recombinant protein to the tentacle anion exchange matrix chromatography medium, and optionally washing the medium, the recombinant protein is eluted by increasing the conductivity and/or reducing the pH of the buffer used to chromatograph the sample. The buffer condition that can selectively elute the recombinant protein will depend, in part, upon the charge of the recombinant protein and the strength of the anionic group.

In one embodiment, the recombinant protein is the recombinant fusion protein etanercept (CAS registry no. 185243-69-0). Etanercept is a recombinant fusion of the soluble extracellular domain of the p75 TNF receptor to the Fc domain of a human IgG1 that is produced in Chinese Hamster Ovary (CHO) cells, and is commercially available from Amgen Inc. (Thousand Oaks, Calif.) under the tradename Enbrel®. The invention is illustrated by way of working examples below using etanercept as the recombinant protein. In one embodiment of the invention, a sample containing etanercept that has been affinity purified using protein A affinity chromatography is subjected to tentacle anion exchange matrix chromatography medium in a buffer at about pH 8. Such a buffer can be any species that buffers well in this pH range such as a phosphate compound or a Tris(hydroxymethyl)aminomethane (Tris) that has been titrated to have about pH 8. A suitable Tris buffer is from 20 to 30 mM Tris:HCl, more preferably about 25 mM Tris:HCl. Optionally, before etanercept is eluted from the tentacle anion exchange matrix chromatography medium, the medium can be washed with the same buffer or a slightly different buffer, as long as etanercept remains bound to the medium. In one aspect, the tentacle anion exchange matrix chromatography medium is washed with one of the above suitable Tris buffers. In one aspect, the buffered solution to wash the column consists essentially of 25 mM Tris at about pH 8. The column can be washed with from 0.5 to 5 column volumes, more typically with from 1 to 3 column volumes.

Following binding of etanercept to the tentacle anion exchange matrix chromatography medium, and optionally washing, it is eluted. Any conditions that will selectively elute the recombinant protein etanercept can be used. In one aspect, etanercept is eluted in an elution buffer at a pH of from about 6.5 to about 8.5, more preferably from about 7.2 to about 7.6. Again, any buffer species that buffers well in this pH range can be used, including but not limited to Tris and phosphate compounds, as well as 3-(N-morpholino) propanesulfonic acid (MOPS), 2-(N-morpholino)ethanesulfonic acid (MES), 2-[4-(2-hydroxyethyl)piperazin-1-yl] ethanesulfonic acid (HEPES), and citrate buffers. For example, the elution buffer can be from about 10 mM to about 50 mM Tris HCL, and about pH 7 to about pH 8. In one aspect, the elution buffer is about 25 mM Tris HCl, pH 7.2 to pH 7.6. One embodiment of an elution buffer is 25 mM Tris HCl, pH 7.2. In addition, the elution buffer can have a salt, such as NaCl and/or sodium sulfate. The concentration of salt can range from 0 mM to 500 mM, or from 100 to 200 mM. Accordingly, another alternative elution buffer is 25 mM Tris HCl, pH 7.5 and NaCl from about 150 mM to about 200 mM.

Using the methods of the invention, the instant inventors have been able to recover very high yields of the desired recombinant protein while eliminating most of the contaminating second protein. Thus, in one aspect, the methods of the invention result in at least 80%, more preferably 85%, even more preferably 90%, and most preferably 95% recovery of the recombinant protein in the eluant. At the same time, at least 70%, more preferably 75%, still more preferably 80%, even more preferably 85% of the second contaminating protein is removed from the eluant, or any combination of the above recoveries and removals can be achieved.

Protein concentration of a sample at any stage of purification can be determined by any suitable method. Such methods are well known in the art and include: 1) colorimetric methods such as the Lowry assay, the Bradford assay, the Smith assay, and the colloidal gold assay; 2) methods utilizing the UV absorption properties of proteins; and 3) visual estimation based on stained protein bands on gels relying on comparison with protein standards of known quantity on the same gel. See e.g. Stoschek (1990), Quantitation of Protein, in *Guide to Protein Purification*, Methods in Enzymol. 182: 50-68.

By "purifying" a recombinant protein, is meant reducing the level of an undesired contaminant. In the methods of the invention, the undesired contaminant is the second protein. The second protein, a complex of the recombinant protein and the second protein, and/or other proteins that may be present in a sample of the recombinant protein being purified, can be monitored by any appropriate means. Preferably, the technique should be sensitive enough to detect contaminants in the range between about 0.5 parts per million (ppm) (calculated as nanograms per milligram of the protein being purified) and 500 ppm. For example, enzyme-linked immunosorbent assay (ELISA), a method well known in the art, may be used to detect contamination of the recombinant protein by the second protein. See e.g. Reen (1994), Enzyme-Linked Immunosorbent Assay (ELISA), in *Basic Protein and Peptide Protocols*, Methods Mol. Biol. 32: 461-466, which is incorporated herein by reference in its entirety. Tentacle anion exchange matrix chromatography may reduce contamination by a second protein at least about twofold, preferably at least about threefold, more preferably at least about fivefold, still more preferably at least about tenfold, even more preferably at least about fifteenfold, most preferably at least about twentyfold. Preferably, contamination of the recombinant protein by the second protein after tentacle anion exchange matrix chromatography is not more than about 100 ppm, more preferably not more than about 80 ppm, more preferably not more than about 60 ppm, more preferably not more than about 40 ppm, more preferably not more than about 20 ppm, more preferably not more than about 10 ppm, more preferably not more than about 5 ppm, more preferably not more than about 1 ppm, and most preferably not more than about 0.5 ppm. Contamination by such a second protein can range from undetectable levels to about 5 ppm or from about 5 ppm to about 400 ppm. If a recombinant protein is being purified for pharmacological use, one of skill in the art will realize that the preferred level of the second protein can depend on the dose of the protein to be administered per patient, with the aim that the patient will not receive more than a certain amount of a contaminating protein per dose. Thus, if the required dose of the protein is decreased, the level of contamination by a second protein may possibly increase.

The invention can be used to purify recombinant proteins, which are proteins that have been produced using genetic engineering techniques. Preferably, the proteins are produced at production scale, which is typically in quantities of several grams at a time. The protein undergoing purification as contemplated by the invention can comprise one or more constant antibody immunoglobulin domain(s) and may, but need not, comprise a single or multiple variable antibody immunoglobulin domain(s). It may be a naturally-occurring protein or a recombinant fusion protein. It may comprise an Fc portion of an antibody. It may also comprise a non-antibody protein.

Examples of recombinant proteins that can be purified with the methods of the invention include proteins comprising amino acid sequences identical to or substantially similar to all or part of one of the following proteins: tumor necrosis factor (TNF), flt3 ligand (WO 94/28391), erythropoeitin, thrombopoeitin, calcitonin, IL-2, angiopoietin-2 (Maisonpierre et al. (1997), *Science* 277(5322): 55-60), ligand for receptor activator of NF-kappa B (RANKL, WO 01/36637), tumor necrosis factor (TNF)-related apoptosis-inducing ligand (TRAIL, WO 97/01633), thymic stroma-derived lymphopoietin, granulocyte colony stimulating factor, granulocyte-macrophage colony stimulating factor (GM-CSF, Australian Patent No. 588819), mast cell growth factor, stem cell growth factor (U.S. Pat. No. 6,204,363), epidermal growth factor, keratinocyte growth factor, megakaryote growth and development factor, RANTES, human fibrinogen-like 2 protein (FGL2; NCBI accession no. NM_00682; Rüegg and Pytela (1995), *Gene* 160:257-62) growth hormone, insulin, insulinotropin, insulin-like growth factors, parathyroid hormone, interferons including $\alpha$-interferons, $\gamma$-interferon, and consensus interferons (U.S. Pat. Nos. 4,695,623 and 4,897,471), nerve growth factor, brain-derived neurotrophic factor, synaptotagmin-like proteins (SLP 1-5), neurotrophin-3, glucagon, interleukins, colony stimulating factors, lymphotoxin-$\beta$, leukemia inhibitory factor, and oncostatin-M. Descriptions of proteins that can be purified according to the inventive methods may be found in, for example, *Human Cytokines: Handbook for Basic and Clinical Research*, all volumes (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook*, Vols. 1 and 2 (Thompson and Lotze eds., Academic Press, San Diego, Calif., 2003).

Additionally the methods of the invention would be useful to purify proteins comprising all or part of the amino acid sequence of a receptor for any of the above-mentioned proteins, an antagonist to such a receptor or any of the above-mentioned proteins, and/or proteins substantially similar to such receptors or antagonists. These receptors and antagonists include: both forms of tumor necrosis factor receptor (TNFR, referred to as p55 and p75, U.S. Pat. Nos. 5,395,760 and 5,610,279), Interleukin-1 (IL-1) receptors (types I and II; EP Patent No. 0460846, U.S. Pat. Nos. 4,968,607, and 5,767,064), IL-1 receptor antagonists (U.S. Pat. No. 6,337,072), IL-1 antagonists or inhibitors (U.S. Pat. Nos. 5,981,713, 6,096,728, and 5,075,222) IL-2 receptors, IL-4 receptors (EP Patent No. 0 367 566 and U.S. Pat. No. 5,856,296), IL-15 receptors, IL-17 receptors, IL-18 receptors, Fc receptors, granulocyte-macrophage colony stimulating factor receptor, granulocyte colony stimulating factor receptor, receptors for oncostatin-M and leukemia inhibitory factor, receptor activator of NF-kappa B (RANK, WO 01/36637 and U.S. Pat. No. 6,271,349), osteoprotegerin (U.S. Pat. No. 6,015,938), receptors for TRAIL (including TRAIL receptors 1, 2, 3, and 4), and receptors that comprise death domains, such as Fas or Apoptosis-Inducing Receptor (AIR).

Enzymatically active proteins or their ligands can also be purified using the invention. Examples include proteins comprising all or part of one of the following proteins or their ligands or a protein substantially similar to one of these: a disintegrin and metalloproteinase domain family members including TNF-alpha Converting Enzyme, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, ligands for any of the above-mentioned enzymes, and numerous other enzymes and their ligands.

The invention can also be used to purify recombinant fusion proteins comprising, for example, any of the above-mentioned proteins. For example, recombinant fusion proteins comprising one of the above-mentioned proteins plus a multimerization domain, such as a leucine zipper, a coiled coil, an Fc portion of an immunoglobulin, or a substantially similar protein, can be produced using the methods of the invention. See e.g. WO94/10308; Lovejoy et al. (1993), *Science* 259:1288-1293; Harbury et al. (1993), *Science* 262:1401-05; Harbury et al. (1994), *Nature* 371:80-83; Hakansson et al. (1999), *Structure* 7:255-64. Specifically included among such recombinant fusion proteins are proteins in which a portion of a protein, including any of the above proteins, is fused to an Fc portion of an antibody. Examples of such proteins are etanercept (a p75 TNFR:Fc) and belatacept (CTLA4:Fc).

The invention can also be used to purify antibodies or portions thereof. The term "antibody" includes reference to both glycosylated and non-glycosylated immunoglobulins of any isotype or subclass or to an antigen-binding region thereof that competes with the intact antibody for specific binding, unless otherwise specified, including human, humanized, chimeric, multi-specific, monoclonal, polyclonal, and oligomers or antigen binding fragments thereof. Antibodies can be any class of immunoglobulin. Also included are proteins having an antigen binding fragment or region such as Fab, Fab', F(ab')$_2$, Fv, diabodies, Fd, dAb, maxibodies, single chain antibody molecules, complementarity determining region (CDR) fragments, scFv, diabodies, triabodies, tetrabodies and polypeptides that contain at least a portion of an immunoglobulin that is sufficient to confer specific antigen binding to a target polypeptide. The term "antibody" is inclusive of, but not limited to, those that are prepared, expressed, created or isolated by recombinant means, such as antibodies isolated from a host cell transfected to express the antibody.

Examples of antibodies that can be purified using the methods of the invention include, but are not limited to, those that recognize any one or a combination of proteins including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235,883) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), *Cytokine Growth Factor Rev.* 13(1): 19-25), C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, Respiratory Syncitial Virus, human immunodeficiency virus (HIV), hepatitis B virus (HBV), *Streptococcus mutans*, and *Staphlycoccus aureus*. Specific examples of known antibodies which can be produced using the methods of the invention include but are not limited to adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, zalutumumab, and zanolimumab.

The protein can be produced by living host cells that have been genetically engineered to produce the protein. Methods of genetically engineering cells to produce proteins are well known in the art. See e.g. Ausubel et al., eds. (1990), Current Protocols in Molecular Biology (Wiley, N.Y.). Such methods include introducing nucleic acids that encode and allow expression of the protein into living host cells. These host cells can be bacterial cells, fungal cells, or, preferably, animal cells grown in culture. Bacterial host cells include, but are not limited to, *Escherichia coli* cells. Examples of suitable *E. coli* strains include: HB101, DH5α, GM2929, JM109, KW251, NM538, NM539, and any *E. coli* strain that fails to cleave foreign DNA. Fungal host cells that can be used include, but are not limited to, *Saccharomyces cerevisiae, Pichia pastoris* and *Aspergillus* cells. A few examples of animal cell lines that can be used are CHO, VERO, BHK, HeLa, Cos, MDCK, 293, 3T3, and WI38. New animal cell lines can be established using methods well know by those skilled in the art (e.g., by transformation, viral infection, and/or selection). Optionally, the protein can be secreted by the host cells into the medium.

After the recombinant protein is produced by the cells, it is harvested. If the protein is secreted by the cells into the culture medium, the cells and debris are removed from the culture medium by any of a number of known techniques such as centrifugation, filtration, and/or flocculation. If the recombinant protein collects inside the cell wall or cell membrane, other known techniques are used to collect and, if necessary, solubilize the recombinant protein for subsequent purification operations.

Typically, affinity chromatography can be used as the first purification step. The recombinant protein in solution is bound to an affinity chromatography medium, the medium is washed, and the recombinant protein is eluted by disrupting the binding of the recombinant protein to the affinity ligand. This eluted sample containing the recombinant protein and the affinity ligand as a contaminant or second protein is then subjected to the methods of the invention on a tentacle anion exchange chromatography medium as described in more detail above.

After the recombinant protein is eluted from the tentacle anion exchange matrix chromatography medium, the eluant containing the recombinant protein can be subjected to a further purification step. Alternatively or in addition, the sample containing the recombinant protein can be subjected to an additional purification step before being subjected to the tentacle anion exchange matrix chromatography in the methods of the invention. Such further purification steps can be a another ion exchange chromatography step (anion and/or cation), another affinity chromatography step, a metal affinity chromatography step, a hydroxyapatite chromatography step, a hydrophobic interaction chromatography step, a gel filtration (size exclusion) chromatography step, and/or a mixed mode chromatography resin. Examples of commercially available resins for such chromatography steps include but are not limited to CHT Ceramic Hydroxyapatite Type II 80 μm particle resin (BioRad Laboratories, Inc., Hercules, Calif.), DEAE Sepharose Fast Flow (GE Healthcare Life Sciences), Eshmuno® Q (EMD Millipore), Fractogel® SO3 (Merck Millipore), Toyopearl 650-M, ToyoScreen Ether-650M, ToyoScreen Phenyl-650M, ToyoScreen PPG-600M (Tosoh Bioscience GmbH), SP Sepharose Fast Flow (GE Healthcare Life Sciences), IMAC Sepharose 6 Fast Flow (GE Healthcare Life Sciences), and Q Sepharose Fast Flow (GE Healthcare Life Sciences). In addition, the recombinant protein can be further purified by filtration. Filtration can be direct (such as block or cake filtration), or can be tangential flow filtration.

In one aspect, the recombinant protein, such as etanercept, is subjected to affinity chromatography over a Protein A chromatography medium. After the recombinant protein is eluted, the sample containing the recombinant protein can be purified over a tentacle anion exchange matrix chromatography medium using the methods of the invention as describe above. However, before or after subjecting the recombinant protein to the tentacle anion exchange matrix chromatography medium, an additional chromatography step can be performed. For example, the recombinant protein can be subjected to hydroxyapatite chromatography in a flow through mode to enhance removal of protein A and other contaminants, or anion or cation exchange chromatography (flow through or bind and elute), or hydrophobic interaction chromatography (flow through or bind and elute).

After the recombinant protein is eluted from the tentacle anion exchange matrix chromatography, the protein can be subjected to further purification steps as noted above before it is formulated, or it can be directly formulated. The term "formulated" means the protein is buffer exchanged, sterilized, bulk-packaged, and/or packaged for a final user. In one embodiment, the recombinant protein is formulated in a pharmaceutical composition. Suitable formulations for pharmaceutical compositions include those described in *Remington's Pharmaceutical Sciences,* 18th ed. 1995, Mack Publishing Company, Easton, Pa.

The following examples are offered by way of illustration and not limitation.

EXAMPLES

Example 1

The goal of these experiments was to effectively remove contaminating Protein A from a recombinant protein preparation while recovering as much recombinant protein as possible. A recombinant protein, etanercept, was expressed in a transformed CHO (Chinese Hamster Ovary) cell culture, and secreted into the medium. After removal of cells from the medium, etanercept was initially purified by running the medium over a Mab Select SuRe™ Protein A resin column (GE Healthcare Life Sciences). Leached protein A was determined using a sandwich ELISA assay. Microtitre plates were coated with a chicken anti-protein A antibody as a capture antibody that was specifically raised against the Mab Select SuRe ligand. After blocking and washing steps, a biotinylated chicken anti-protein A antibody was used as the detection antibody. The amount of leached protein A in the sample after initial purification over the Mab Select SuRe™ Protein A resin column ranged from about 1 ppm to about 20 ppm.

In the following experiments, the initially purified etanercept was run over a CHT Ceramic Hydroxyapatite Type II 80 μm particle resin (BioRad Laboratories, Inc., Hercules, Calif.) under the following conditions. The yield of etanercept, expressed as a %, was determined using ELISA on the pre and post sample collection. The amount of leached protein A reduction, also expressed as a %, was determined before and after Hydroxyapatite chromatography using the sandwich ELISA described above.

| | | | | | | | |
|---|---|---|---|---|---|---|---|
| | | | Resin: Hydroxyapatite | | | | |
| Equil. Buffer | Load Cond. (mS/cm) | Load pH | Wash Buffer | Elut. pH | Elut. Buffer Cond. (mS/cm) | Yield (%) | Leached Protein A Red. (%) |
| 25 mM Sodium Phosphate, pH 6.8 | 3.02 | 6.69 | 25 mM Sodium Phosphate, pH 6.8 | 6.8 | 2.9 | 96.8 | 20.3 |
| 25 mM Sodium Phosphate, pH 6.8 | 2.96 | 6.74 | 25 mM Sodium Phosphate, pH 6.8 | 6.83 | 2.9 | 93 | 51.4 |
| 25 mM Sodium Phosphate, pH 6.8 | 2.98 | 6.72 | 25 mM Sodium Phosphate, pH 6.8 | 6.83 | 2.9 | 96.4 | 11.5 |
| 25 mM Sodium Phosphate, pH 6.8 | 2.98 | 6.72 | 25 mM Sodium Phosphate, pH 6.8 | 6.83 | 2.9 | 95.9 | 16.7 |
| 25 mM Sodium Phosphate, pH 6.8 | 2.98 | 6.72 | 25 mM Sodium Phosphate, pH 6.8 | 6.83 | 2.9 | 96.8 | 17.9 |
| 25 mM Sodium Phosphate, pH 6.8 | 2.98 | 6.72 | 25 mM Sodium Phosphate, pH 6.8 | 6.83 | 2.9 | 93.6 | 17.9 |
| 25 mM Sodium Phosphate, pH 6.8 | 2.98 | 6.72 | 25 mM Sodium Phosphate, pH 6.8 | 6.83 | 2.9 | 95.9 | 11.5 |
| 25 mM Sodium Phosphate, pH 6.8 | 2.81 | 6.76 | 25 mM Sodium Phosphate, pH 6.8 | 6.72 | 2.9 | 94 | 19.4 |

-continued

| | | | | | Elut. | | Leached |
| | Load | | | | Buffer | | Protein A |
| | Cond. | Load | | Elut. | Cond. | Yield | Red. |
| Equil. Buffer | (mS/cm) | pH | Wash Buffer | pH | (mS/cm) | (%) | (%) |
|---|---|---|---|---|---|---|---|
| 25 mM Sodium Phosphate, pH 6.8 | 2.81 | 6.76 | 25 mM Sodium Phosphate, pH 6.8 | 6.72 | 2.9 | 92 | 29 |
| 25 mM Sodium Phosphate, pH 6.8 | 2.81 | 6.76 | 25 mM Sodium Phosphate, pH 6.8 | 6.72 | 2.9 | 95.2 | 9.68 |
| 25 mM Sodium Phosphate, pH 6.8 | 2.81 | 6.76 | 25 mM Sodium Phosphate, pH 6.8 | 6.72 | 2.9 | 92.7 | 30.6 |
| 25 mM Sodium Phosphate, pH 6.8 | 2.81 | 6.76 | 25 mM Sodium Phosphate, pH 6.8 | 6.72 | 2.9 | 95.3 | 19.4 |
| 25 mM Sodium Phosphate, pH 6.8 | 3.16 | 6.72 | 25 mM Sodium Phosphate, pH 6.8 | 6.82 | 2.9 | 96.1 | 40.7 |
| 25 mM Sodium Phosphate, pH 6.8 | 3.16 | 6.72 | 25 mM Sodium Phosphate, pH 6.8 | 6.82 | 2.9 | 97.3 | 39.5 |
| 100 mM Sodium Acetate, 100 mM Sodium Chloride, 3M Sodium Phosphate, pH 6.8 | 15.58 | 6.87 | 100 mM Sodium Acetate, 100 mM Sodium Chloride, 3M Sodium Phosphate, pH 6.8 | 6.84 | 13.6 | 92 | 77.6 |
| 5 mM Sodium Phosphate | not recorder | 6.9 | 5 mM Sodium Phosphate | 6.89 | 0.661 | 93.1 | 31.1 |
| 10 mM Sodium Phosphate | 5.54 | 6.94 | 10 mM Sodium Phosphate | 6.85 | 1.25 | 97.3 | 12.5 |
| 50 mM MES, 5 mM Sodium Phophate | 5.92 | 6.75 | 50 mM MES, 5 mM Sodium Phosphate | 6.81 | 2.88 | 98.7 | 12.7 |
| 100 mM Sodium Acetate, 3 mM Sodium Phosphate, 65 mM Sodium Chloride, pH 6.75, cond 14.77 | 4.33 | 6.77 | 100 mM Sodium Acetate, 3 mM Sodium Phosphate, 65 mM Sodium Chloride, pH 6.75, cond 14.77 | 6.75 | 14.77 | 93.6 | 50 |
| 100 mM Sodium Chloride, 100 mM Sodium Acetate, 3 mM Sodium Phosphate, pH 6.8 | 9.68 | 6.96 | 100 mM Sodium Chloride, 100 mM Sodium Acetate, 9 mM Sodium Phosphate, pH 6.8 | 6.73 | 17.96 | 80.8 | 61.8 |
| 100 mM Sodium Chloride, 100 mM Sodium Acetate, 3 mM Sodium Phosphate, pH 6.8 | 8.13 | 7 | 100 mM Sodium Chloride, 100 mM Sodium Acetate, 12 mM Sodium Phosphate, pH 6.8 | 6.8 | 18.99 | 86.9 | 57 |
| 100 mM Sodium Chloride, 100 mM Sodium Acetate, 3 mM Sodium Phosphate, pH 6.8 | 7.64 | 6.9 | 100 mM Sodium Chloride, 100 mM Sodium Acetate, 6 mM Sodium Phosphate, pH 6.8 | 6.8 | 18.46 | 97.1 | 82.4 |
| 100 mM Sodium Chloride, 100 mM Sodium Acetate, 3 mM Sodium Phosphate, pH 6.8 | 9.72 | 6.91 | 100 mM Sodium Chloride, 100 mM Sodium Acetate, 9 mM Sodium Phosphate, pH 6.8 | 6.73 | 17.96 | 93.3 | 63.6 |
| 100 mM Sodium Chloride, 100 mM Sodium Acetate, 3 mM Sodium Phosphate, pH 6.8 | not recorder | not recorded | 100 mM Sodium Chloride, 100 mM Sodium Acetate, 6 mM Sodium Phosphate, pH 6.8 | 6.8 | 18.46 | 92.9 | 65.5 |
| 100 mM Sodium Chloride, 100 mM Sodium Acetate, 3 mM Sodium Phosphate, pH 6.8 | 14.16 | 6.84 | 100 mM Sodium Chloride, 100 mM Sodium Acetate, 12 mM Sodium Phosphate, pH 6.8 | 6.8 | 18.99 | 88.3 | 30.3 |
| 100 mM Sodium Chloride, 100 mM Sodium Acetate, 3 mM Sodium Phosphate, pH 6.8 | 8.07 | 6.94 | 100 mM Sodium Chloride, 100 mM Sodium Acetate, 6 mM Sodium Phosphate, pH 6.8 | 6.8 | 18.46 | 98.8 | 61.8 |

-continued

| | | | Resin: Hydroxyapatite | | | | |
|---|---|---|---|---|---|---|---|
| Equil. Buffer | Load Cond. (mS/cm) | Load pH | Wash Buffer | Elut. pH | Elut. Buffer Cond. (mS/cm) | Yield (%) | Leached Protein A Red. (%) |
| 100 mM Sodium Chloride, 100 mM Sodium Acetate, 3 mM Sodium Phosphate, pH 6.8 | 14.2 | 6.88 | 100 mM Sodium Chloride, 100 mM Sodium Acetate, 6 mM Sodium Phosphate, pH 6.8 | 6.8 | 18.46 | 90.5 | 23.6 |
| 100 mM Sodium Chloride, 100 mM Sodium Acetate, 3 mM Sodium Phosphate, pH 6.8 | 13.7 | 6.83 | 100 mM Sodium Chloride, 100 mM Sodium Acetate, 12 mM Sodium Phosphate, pH 6.8 | 6.8 | 18.99 | 79.3 | 58.2 |
| 100 mM Sodium Chloride, 100 mM Sodium Acetate, 3 mM Sodium Phosphate, pH 6.8 | 7.57 | 6.9 | 100 mM Sodium Chloride, 100 mM Sodium Acetate, 12 mM Sodium Phosphate, pH 6.8 | 6.8 | 18.99 | 91.5 | 84.8 |
| 100 mM Sodium Chloride, 100 mM Sodium Acetate, 3 mM Sodium Phosphate, pH 6.8 | 9.88 | 6.89 | 100 mM Sodium Chloride, 100 mM Sodium Acetate, 9 mM Sodium Phosphate, pH 6.8 | 6.73 | 17.96 | 88.4 | 63 |
| 100 mM Sodium Chloride, 100 mM Sodium Acetate, 3 mM Sodium Phosphate, pH 6.8 | 8.16 | 6.92 | 100 mM Sodium Chloride, 100 mM Sodium Acetate, 12 mM Sodium Phosphate, pH 6.8 | 6.8 | 18.99 | 98.7 | 55.5 |
| 100 mM Sodium Chloride, 100 mM Sodium Acetate, 3 mM Sodium Phosphate, pH 6.8 | not recorded | not recorded | 100 mM Sodium Chloride, 100 mM Sodium Acetate, 12 mM Sodium Phosphate, pH 6.8 | 6.8 | 18.99 | 88.4 | 9.09 |
| 100 mM Sodium Chloride, 100 mM Sodium Acetate, 25 mM Sodium Phosphate, pH 6.8 | 16.15 | 6.72 | 100 mM Sodium Chloride, 100 mM Sodium Acetate, 25 mM Sodium Phosphate, pH 6.8 | 6.77 | 21.1 | 98.5 | −1.5 |
| 100 mM Sodium Chloride, 100 mM Sodium Acetate, 12 mM Sodium Phosphate, pH 6.8 | 15.63 | 6.76 | 100 mM Sodium Chloride, 100 mM Sodium Acetate, 12 mM Sodium Phosphate, pH 6.8 | 6.8 | 21.8 | 97.9 | 13.2 |
| 100 mM Sodium Chloride, 100 mM Sodium Acetate, 3 mM Sodium Phosphate, pH 6.8 | not recorded | not recorded | 100 mM Sodium Chloride, 100 mM Sodium Acetate, 3 mM Sodium Phosphate, pH 6.8 | 6.82 | 20 | 99 | 67.6 |
| 100 mM Sodium Chloride, 100 mM Sodium Acetate, 25 mM Sodium Phosphate, pH 6.8 | 9.88 | 6.96 | 100 mM Sodium Chloride, 100 mM Sodium Acetate, 25 mM Sodium Phosphate, pH 6.8 | 6.77 | 21.1 | 102 | −1.5 |
| 100 mM Sodium Chloride, 100 mM Sodium Acetate, 12 mM Sodium Phosphate, pH 6.8 | 8.83 | 6.88 | 100 mM Sodium Chloride, 100 mM Sodium Acetate, 12 mM Sodium Phosphate, pH 6.8 | 6.8 | 21.8 | 94.6 | 42.6 |
| 100 mM Sodium Chloride, 100 mM Sodium Acetate, 3 mM Sodium Phosphate, pH 6.8 | 8.24 | 6.86 | 100 mM Sodium Chloride, 100 mM Sodium Acetate, 3 mM Sodium Phosphate, pH 6.8 | 6.82 | 20 | 87.4 | 82.4 |

Using hydroxyapatite chromatography in a flow through mode, it was possible to remove over 80% of the leached protein A while recovering over 90% of the etanercept protein.

Example 2

Using the relatively weak anion exchange resin DEAE Sepharose Fast Flow (GE Healthcare Life Sciences), a variety of different buffers and elution conditions was explored as detailed in the below table. Etanercept and protein A concentrations were determined as in Example 1.

| Test Resin: DEAE Sepharose FF | | | | | | | |
|---|---|---|---|---|---|---|---|
| Mode/ Equilibration and Wash Buffer | Load Cond. (mS/cm) | Load pH | Elution Buffer | Elution Buffer Conductivity (mS/cm) | Elution Flow Rate | Yield (%) | Leached Protein A Reduction (%) |
| Bind/Elute/ 25 mM Tris, pH 8 | 5.2 | 8 | 25 mM Tris, 150 mM NaCl, pH 7.4 | 17.14 | 0.5 mL/min | 80 | 27.9 |
| Bind/Elute/ 25 mM Tris, pH 8 | 5.2 | 8 | 25 mM Tris, 150 mM NaCl, pH 7.4 | 17.14 | 0.5 mL/min | 85 | 26.2 |
| Bind/Elute/ 25 mM Tris, pH 8 | 5.2 | 8 | 25 mM Tris, 175 mM NaCl, pH 7.5 | 20 | 0.5 mL/min | 85 | 15.1 |
| Bind/Elute/ 25 mM Tris, pH 8 | 5.2 | 8 | 25 mM Tris, 175 mM NaCl, pH 7.5 | 20 | 0.5 mL/min | 84 | 46.3 |
| Bind/Elute/ 25 mM Tris, pH 8 | 5.2 | 8 | 25 mM Tris, 125 mM NaCl, pH 7.5 | 13.7 | 0.5 mL/min | 86 | 55.9 |
| Bind/Elute/ 25 mM Tris, pH 8 | 5.2 | 8 | 25 mM Tris, 125 mM NaCl, pH 7.5 | 13.7 | 0.5 mL/min | 85 | 61.3 |
| Bind/Elute/ 25 mM Tris, pH 8 | 5.2 | 8 | 25 mM Tris, 100 mM NaCl, pH 7.4 | 13.3 | 0.5 mL/min | 72.4 | 96.3 |
| Bind/Elute/ 25 mM Tris, pH 8 | 5.2 | 8 | 25 mM Tris, 100 mM NaCl, pH 7.4 | 13.3 | 0.5 mL/min | 74.7 | 93.2 |
| Bind/Elute/ 25 mM Tris, pH 8 | 5.2 | 7.94 | 25 mM Tris, 250 mM NaCl, pH 7.4 | 29.2 | 100 cm/hr | 94.1 | 1.75 |
| Bind/Elute/ 25 mM Tris, pH 8 | 5.2 | 7.94 | 25 mM Tris, 100 mM NaCl, pH 7.4 | 13.6 | 100 cm/hr | 77.4 | 94.6 |
| Bind/Elute/ 25 mM Tris, pH 8 | 5.2 | 7.94 | 25 mM Tris, 100 mM NaCl, pH 7.4 | 13.6 | 100 cm/hr | 79.8 | 94.5 |
| FlowThrough/ 55 mM Sodium Phosphate | 6.7 | 11.28 | Not applicable | not recorded | Not applicable | 95 | 25 |
| Bind/Elute/ 25 mM Tris pH 7.4 | 5 | 7.4 | 25 mM Tris, 100 mM NaCl pH 7.4 | 12.14 | 25 cm/hr | 64.6 | 88.2 |
| Bind/Elute/ 25 mM Tris pH 7.4 | 5 | 7.4 | 25 mM Tris, 150 mM NaCl pH 7.4 | 16.7 | 25 cm/hr | 87.1 | 9.8 |
| Bind/Elute/ 25 mM Tris pH 7.4 | 5 | 7.4 | 25 mM Tris, 200 mM NaCl pH 7.4 | 21.2 | 25 cm/hr | 87.3 | −2 |
| Bind/Elute/ 25 mM Tris pH 7.4 | 4 | 7.6 | 25 mM Tris, 100 mM NaCl pH 7.4 | 12.14 | 25 cm/hr | 72.6 | 94.1 |
| Bind/Elute/ 25 mM Tris pH 7.4 | 4 | 7.6 | 25 mM Tris, 150 mM NaCl pH 7.4 | 16.7 | 25 cm/hr | 89.5 | 23.5 |
| Bind/Elute/ 25 mM Tris pH 7.4 | 4 | 7.6 | 25 mM Tris, 200 mM NaCl pH 7.4 | 21.2 | 25 cm/hr | 88.2 | 11.8 |
| Bind/Elute/ 25 mM Tris pH 7.4 | 5 | 7.4 | 25 mM Tris, 165 mM NaCl pH 7.4 | 17.98 | 25 cm/hr | 87 | 11.3 |
| Bind/Elute/ 25 mM Tris pH 7.4 | 5 | 7.4 | 25 mM Tris, 165 mM NaCl pH 7.4 | 17.98 | 25 cm/hr | 84.2 | 9.43 |

As can be seen from the data above, DEAE Sepharose can remove a high percentage of leached Protein A under certain conditions. However, under those conditions the recovery of the recombinant protein etanercept was impacted.

Example 3

In this experiment, a different anion exchange resin was tested for its ability to remove protein A while maintaining a high recovery rate. The resin was Eshmuno® Q, which is available from EMD Millipore, a division of Merck KGaA, Darmstadt, Germany. All runs were in a bind and elute mode.

| Resin: Eshmuno Q | | | | | |
|---|---|---|---|---|---|
| Equilibration and Wash Buffer | Load Cond. (mS/cm) | Load pH | Elution Buffer and Conductivity | Yield (%) | Leached Protein A Reduction (%) |
| 25 mM Tris, pH 8, cond. 5 mS/cm | 5 | 8 | 25 mM Tris, pH 7.4, cond. 21 mS/cm | 93.8 | 55.6 |
| 25 mM Tris, pH 8, cond. 5 mS/cm | 5 | 8 | 25 mM Tris, pH 7.4, cond. 21 mS/cm | 94.4 | 60.8 |
| 25 mM Tris, pH 8, cond. 5 mS/cm | 5 | 8 | 25 mM Tris, pH 7.4, cond. 21 mS/cm | 92 | 64.7 |
| 25 mM Tris, pH 8, cond. 5 mS/cm | 5 | 8 | 25 mM Tris, pH 7.4, cond. 21 mS/cm | 92.5 | 63.3 |

Although the recovery of etanercept was high using this resin, reduction of Protein A was not sufficient.

Example 4

The strong cation exchanger Fractogel® SO3 (Merck Millipore) was also tested under a large variety of conditions detailed in the below table. For all conditions, the mode was bind and elute, equilibration and wash buffer was 75 mM Sodium Acetate, and elution was at 150 cm/hr in a 100 mM Sodium Acetate buffer at the indicated salt concentration (expressed in mM).

| Test Resin: Fractogel SO3 | | | | | | |
|---|---|---|---|---|---|---|
| Load pH | Load Cond. (mS/cm) | Elution pH | Elution NaCl (mM) | Elution Buffer Cond. (mS/cm) | Yield (%) | Leached Protein A Reduction (%) |
| 6 | 6 | 5 | 75 | 15.4 | 54.7 | 74 |
| 6 | 6 | 6 | 225 | 28.1 | 92.8 | −26 |
| 5.25 | 5 | 5.5 | 150 | 21.5 | 112.2 | 3.16 |
| 4.5 | 6 | 5 | 75 | 15.4 | 77.5 | 70.7 |
| 6 | 4 | 6 | 75 | 15.24 | 95.8 | 40 |
| 6 | 6 | 5 | 75 | 15.4 | 61.1 | 79 |
| 4.5 | 4 | 5 | 75 | 15.4 | 69.7 | 65.8 |
| 6 | 4 | 5 | 75 | 15.4 | 76.4 | 35.8 |
| 6 | 4 | 6 | 225 | 28.1 | 107.7 | −12 |
| 6 | 6 | 6 | 75 | 15.24 | 85.3 | 73 |
| 4.5 | 6 | 6 | 225 | 28.1 | 111.9 | −17 |
| 6 | 4 | 5 | 75 | 15.4 | 69.8 | 52.6 |
| 4.5 | 4 | 6 | 75 | 15.24 | 105.1 | 32.9 |
| 4.5 | 4 | 6 | 225 | 28.1 | 107.4 | −41 |
| 6 | 6 | 6 | 225 | 28.1 | 91.5 | −38 |
| 5.25 | 5 | 5.5 | 150 | 21.5 | 109.2 | 8.42 |
| 4.5 | 4 | 5 | 225 | 28.9 | 107.3 | −13 |
| 4.5 | 6 | 5 | 225 | 28.9 | 108.6 | 8.7 |
| 6 | 6 | 5 | 225 | 28.9 | 89.5 | −6 |
| 4.5 | 4 | 5 | 75 | 15.4 | 66.3 | 69.6 |
| 4.5 | 6 | 5 | 75 | 15.4 | 73.1 | 76.1 |
| 6 | 4 | 5 | 225 | 28.9 | 112.4 | −1.1 |
| 6 | 6 | 6 | 75 | 15.24 | 81.6 | 79 |
| 5.25 | 5 | 5.5 | 150 | 21.5 | 109.4 | 26.3 |
| 4.5 | 6 | 6 | 75 | 15.24 | 97.9 | 44.6 |
| 4.5 | 6 | 5 | 225 | 28.9 | 105.6 | 7.61 |
| 4.5 | 6 | 6 | 225 | 28.1 | 103.9 | 3.26 |
| 4.5 | 4 | 6 | 75 | 15.24 | 100.9 | 34.2 |
| 6 | 4 | 6 | 225 | 28.1 | 106 | −5.3 |
| 6 | 4 | 6 | 75 | 15.24 | 98 | 41.1 |
| 4.5 | 6 | 6 | 75 | 15.24 | 103.8 | 50 |
| 6 | 6 | 5 | 225 | 28.9 | 89.5 | −16 |
| 4.5 | 4 | 5 | 225 | 28.9 | 108.5 | 1.27 |
| 4.5 | 4 | 6 | 225 | 28.1 | 110.1 | −13 |
| 6 | 4 | 5 | 225 | 28.9 | 108.1 | −5.3 |
| 5.25 | 5 | 5.5 | 150 | 21.5 | 108.1 | 7.37 |
| 4.97 | 4.43 | 5.7 | 85 | 16 | 96.1 | 49 |
| 4.97 | 4.43 | 5.7 | 85 | 16 | 99.6 | 44.4 |
| 5.01 | 4.51 | 5.7 | 85 | 17.98 | 101.4 | 27.5 |
| 5 | 4.49 | 5.7 | 85 | 15.82 | 94.23 | 50 |
| 5 | 4.49 | 5.7 | 85 | 15.82 | 91.82 | 27.2 |
| 5 | 4.48 | 5.7 | 85 | 15.82 | 91.56 | 53.8 |
| 4.51 | 5 | 5 | 106 | 17.41 | 72.54 | 45.4 |
| 5.01 | 4.51 | 5.7 | 85 | 17.98 | 97.4 | 48.8 |
| 5.01 | 4.51 | 5.7 | 85 | 17.98 | 97.6 | 47.5 |
| 5 | 4.4 | 5.7 | 85 | 17.45 | 96.2 | 14.5 |
| 5.01 | 4.47 | 5.3 | 170 | 23.5 | 95.3 | 20.2 |
| 5.01 | 4.47 | 5.5 | 135 | 20.5 | 95.6 | 26.9 |
| 5.01 | 4.47 | 5.3 | 100 | 17.31 | 87 | 47.7 |
| 5.01 | 4.47 | 5.7 | 100 | 17.17 | 91.5 | 48 |
| 5.01 | 4.47 | 5.5 | 135 | 20.5 | 94.8 | 26.9 |
| 5.01 | 4.47 | 5.7 | 170 | 23.5 | 97 | 26.9 |
| 5.03 | 4.56 | 5.7 | 85 | 16.07 | 84.02 | 50.4 |
| 5.02 | 4.54 | 5.7 | 85 | 16.07 | 86.1 | 52 |
| 5.1 | 4.45 | 5.7 | 85 | 14.97 | 83.9 | 56.9 |
| 5.028 | 4.67 | 5.7 | 85 | 15.21 | 82.9 | 43.4 |
| 5.07 | 4.5 | 5.7 | 85 | 14.99 | 80.8 | 40.5 |
| 5.09 | 4.5 | 5.7 | 85 | 14.99 | 86.6 | 40.5 |

Some of the yields were calculated to be over 100% in this experiment. However, this reflects a difference in the procedure and calculation of the load, as opposed to a difference in the function of the chromatography step, and for purposes of the run were taken as a 100% yield. Although the yield was overall very high with this resin, removal of leached protein A was insufficient under all conditions tested.

Example 5

In this experiment, several different hydrophobic interaction chromatography resins were examined for their ability to remove leached protein A while maintaining a high level of recovery of the recombinant protein. The columns were equilibrated and washed with Sodium Citrate, pH 3.8 (except for the last HIC-ToyoScreen Phenyl-650 run which was done at a higher load pH and washed with 75 mM Sodium Citrate, pH 5.5). Each of the columns was loaded and run in a flow through mode at about 1 ml/minute, and washed with about 3 column volumes.

| | | | | Resin: HIC | | | |
|---|---|---|---|---|---|---|---|
| Resin Subtype | Load Cond. (mS/cm) | Load pH | Elution pH | Elution buffer | Elution Buffer Cond. (mS/cm) | Yield (%) | Leached Protein A Reduction (%) |
| Toyopearl 650-M | 11.75 | 3.8 | 3.8 | 75 mM Sodium Citrate, pH 3.8 | 5.59 | 46.9 | 89 |
| ToyoScreen Ether-650M | 11.41 | 3.82 | 3.8 | 75 mM Sodium Citrate, pH 3.8 | 5.77 | 62.6 | 13 |
| ToyoScreen Ether-650M | 11.22 | 3.82 | 3.8 | 75 mM Sodium Citrate, pH 3.8 | 5.78 | 105.2 | 9.57 |
| ToyoScreen Phenyl-650M | 11.48 | 3.81 | 3.9 | 75 mM Sodium Citrate, pH 3.8 | 5.78 | 104.4 | 11 |
| ToyoScreen Phenyl-650M | 15.03 | 3.76 | 3.8 | 150 mM Sodium Citrate, pH 3.8 | 10.19 | 104.3 | 6.73 |
| ToyoScreen Phenyl-650M | 20.7 | 3.71 | 3.7 | 300 mM Sodium Citrate, pH 3.8 | 17.4 | 103.8 | 4.5 |
| ToyoScreen Phenyl-650M | 8.54 | 3.15 | 3.1 | 75 mM Sodium Citrate, pH 3 | 3.3 | 85.7 | −4.8 |
| ToyoScreen Phenyl-650M | 17.78 | 5.55 | 5.6 | 75 mM Sodium Citrate, pH 5.5 | 12.76 | 105.3 | −1.7 |
| ToyoScreen PPG-600M | 11.5 | 3.81 | 3.9 | 75 mM Sodium Citrate, pH 3.8 | 5.78 | 105.3 | 9.57 |

Although it was possible to recover high amounts of the recombinant protein etanercept, very little reduction of Protein A was observed under these conditions.

Example 6

The strong anion exchanger, Q Sepharose Fast Flow (GE Healthcare Life Sciences) was also tested under a number of conditions as illustrated in the below table.

| | | | | Resin: Q Sepharose FF | | | |
|---|---|---|---|---|---|---|---|
| Equilibration and Wash Buffer | Load Cond. (mS/cm) | Load pH | Elution Buffer and Elution pH | Elution Buffer Cond. (mS/cm) | Yield (%) | Leached Protein A Reduction (%) | |
| 25 mM Tris, pH 8 | 5.2 | 8 | 25 mM Tris, 175 mM NaCl, pH 7.4 | 20 | 81 | 47.1 | |
| 25 mM Tris, pH 8 | 5.2 | 8 | 25 mM Tris, 175 mM NaCl, pH 7.4 | 20 | 80 | 33 | |
| 25 mM Tris, pH 8 | 5.2 | 8 | 25 mM Tris, 165 mM NaCl, pH 7.4 | 19.7 | 78 | 47.6 | |
| 25 mM Tris, pH 8 | 5.2 | 8 | 25 mM Tris, 165 mM NaCl, pH 7.4 | 19.7 | 77 | 40.4 | |
| 25 mM Tris, pH 8 | 5.2 | 8 | 25 mM Tris, 150 mM NaCl, pH 7.4 | 18.2 | 79 | 59.6 | |
| 25 mM Tris, pH 8 | 5.2 | 8 | 25 mM Tris, 150 mM NaCl, pH 7.4 | 18.2 | 74 | 59.1 | |
| 25 mM Tris pH 7.4 | 4 | 7.4 | 25 mM Tris, 106 mM NaCl pH 7.4 | 12.85 | 44.5 | 100 | |
| 25 mM Tris pH 7.4 | 4 | 7.4 | 25 mM Tris, 150 mM NaCl pH 7.4 | 17.11 | 75.1 | 77.4 | |
| 25 mM Tris pH 7.4 | 4 | 7.4 | 25 mM Tris, 165 mM NaCl pH 7.4 | 18 | 78.5 | 56.6 | |
| 25 mM Tris pH 7.4 | 4 | 7.4 | 25 mM Tris, 150 mM NaCl pH 7.4 | 17.11 | 75.5 | 50.9 | |
| 25 mM Tris pH 7.4 | 4 | 7.4 | 25 mM Tris, 165 mM NaCl pH 7.4 | 18 | 80.2 | 77.4 | |

-continued

| Resin: Q Sepharose FF | | | | | | |
|---|---|---|---|---|---|---|
| Equilibration and Wash Buffer | Load Cond. (mS/cm) | Load pH | Elution Buffer and Elution pH | Elution Buffer Cond. (mS/cm) | Yield (%) | Leached Protein A Reduction (%) |
| 25 mM Tris pH 7.4 | 4 | 7.4 | 25 mM Tris, 180 mM NaCl pH 7.4 | 20.3 | 90.7 | 34 |
| 25 mM Tris pH 7.4 | 4 | 7.4 | 25 mM Tris, 190 mM NaCl pH 7.4 | 21.8 | 89.8 | 22.6 |
| 25 mM Tris pH 7.4 | 4 | 7.6 | 25 mM Tris, 165 mM NaCl pH 7.4 | 18 | 81.3 | 64.7 |
| 25 mM Tris pH 7.4 | 4 | 7.6 | 25 mM Tris, 200 mM NaCl pH 7.4 | 21.2 | 86.6 | 17.6 |
| 25 mM Tris pH 7.4 | 5 | 7.4 | 25 mM Tris, 150 mM NaCl pH 7.4 | 16.29 | 80 | 67.9 |
| 25 mM Tris pH 7.4 | 5 | 7.4 | 25 mM Tris, 150 mM NaCl pH 7.4 | 16.29 | 80.4 | 67.9 |
| 25 mM Tris pH 7.4 | 5 | 7.4 | 25 mM Tris, 165 mM NaCl pH 7.4 | 17.98 | 87.9 | 39.6 |
| 25 mM Tris pH 7.4 | 5 | 7.4 | 25 mM Tris, 165 mM NaCl pH 7.4 | 17.98 | 86.6 | 45.3 |
| 25 mM Tris pH 7.4 | 5 | 7.4 | 25 mM Tris, 175 mM NaCl pH 7.4 | 19.4 | 88 | 28.3 |
| 25 mM Tris pH 7.4 | 5 | 7.4 | 25 mM Tris, 175 mM NaCl pH 7.4 | 19.4 | 88.3 | 26.4 |
| 25 mM Tris pH 7.4 | 4 | 7.6 | 25 mM Tris, 165 mM NaCl pH 7.4 | 17.98 | 82.7 | 61.1 |
| 25 mM Tris pH 7 | 6 | 7 | 25 mM Tris, 165 mM NaCl pH 7 | 18.67 | 85.9 | 29.8 |
| 25 mM Sodium Phosphate pH 6.8 | 6 | 6.8 | 25 mM Sodium Phosphate, 165 mM NaCl, pH 6.9 | 18.53 | 82.8 | 31.6 |
| 25 mM Sodium Phosphate pH 6.6 | 6 | 6.6 | 25 mM Sodium Phosphate, 165 mM NaCl, pH 6.6 | 18.21 | 82.2 | 28.6 |

With Q Sepharose FF, both yield and removal of leached protein A was not sufficient under any one condition.

Example 7

A number of other resins were evaluated in initial experiments (not shown), but showed little promise of achieving the desired level of purification and recovery. Hence, they were not subjected to the optimization experiments shown here.

Example 8

In this experiment, Fractogel® EMD TMAE HiCap (EMD Millipore) was tested under a variety of conditions as detailed in the below table. All of the runs below were done in a bind and elute mode, and washed with 10, 5, or 3 column volumes.

| Resin: Fractogel ® EMD TMAE HiCap | | | | | | | | |
|---|---|---|---|---|---|---|---|---|
| Equil. Buffer | Wash Buffer | Load Cond. (mS/cm) | Load pH | Elution Buffer | Elution Buffer pH | Elution Buffer Cond. (mS/cm) | Yield (%) | Leach Prot A Reduct (%) |
| 25 mM Tris, pH 8 | 25 mM Tris, pH 8 | 4.9 | 8 | 25 mM Tris, 150 mM NaCl, pH 7.4 | 7.4 | 19.3 | 83.9 | 83.8 |

-continued

| | | | | | | | | |
|---|---|---|---|---|---|---|---|---|
| Resin: Fractogel ® EMD TMAE HiCap | | | | | | | | |
| Equil. Buffer | Wash Buffer | Load Cond. (mS/cm) | Load pH | Elution Buffer | Elution Buffer pH | Elution Buffer Cond. (mS/cm) | Yield (%) | Leach Prot A Reduct (%) |
| 25 mM Tris, pH 8 | 25 mM Tris, pH 8 | 4.9 | 8 | 25 mM Tris, 165 mM NaCl, pH 7.6 | 7.6 | 18.6 | 82.7 | 72.8 |
| 25 mM Tris, pH 8 | 25 mM Tris, pH 8 | 4.9 | 8 | 25 mM Tris, 165 mM NaCl, pH 7.6 | 7.6 | 18.6 | 80.2 | 71.4 |
| 25 mM Tris, pH 8 | 25 mM Tris, pH 8 | 4.9 | 8 | 25 mM Tris, 175 mM NaCl, pH 7.5 | 7.5 | 19.3 | 81.8 | 66.7 |
| 25 mM Tris, pH 8 | 25 mM Tris, pH 8 | 4.9 | 8 | 25 mM Tris, 175 mM NaCl, pH 7.5 | 7.5 | 19.3 | 81.8 | 66.1 |
| 25 mM Tris, pH 8 | 25 mM Tris, pH 8 | 4.9 | 8 | 25 mM Tris, 175 mM NaCl, pH 7.5 | 7.5 | 19.3 | 83.2 | 65.7 |
| 25 mM Tris, pH 8 | 25 mM Tris, pH 8 | 4.9 | 8 | 25 mM Tris, 175 mM NaCl, pH 7.5 | 7.5 | 19.3 | 84.5 | 66.7 |
| 25 mM Tris, pH 8 | 25 mM Tris, pH 8 | 4.9 | 8 | 25 mM Tris, 165 mM NaCl, pH 7.6 | 7.6 | 18.6 | 84.6 | 80.6 |
| 25 mM Tris, pH 8 | 25 mM Tris, pH 8 | 4.9 | 8 | 25 mM Tris, 165 mM NaCl, pH 7.6 | 7.6 | 18.6 | 84 | 73.2 |
| 25 mM Tris, pH 8 | 25 mM Tris, pH 8 | 4.9 | 8 | 25 mM Tris, 150 mM NaCl, pH 7.4 | 7.46 | 15.7 | 88.4 | 87.1 |
| 25 mM Tris, pH 8 | 25 mM Tris, pH 8 | 4.9 | 8 | 25 mM Tris, 150 mM NaCl, pH 7.4 | 7.46 | 15.7 | 90.3 | 87.3 |
| 25 mM Tris, pH 8 | 25 mM Tris, pH 8 | 4.9 | 8.1 | 25 mM Tris, 150 mM NaCl, pH 7.4 | 7.41 | 16.68 | 72.7 | 83.7 |
| 25 mM Tris, pH 8 | 25 mM Tris, pH 8 | 4.9 | 8.1 | 25 mM Tris, 150 mM NaCl, pH 7.4 | 7.41 | 16.68 | 72.6 | 78.6 |
| 25 mM Tris, pH 8 | 25 mM Tris, pH 8 | 5.2 | 7.9 | 25 mM Tris, 250 mM NaCl, pH 7.4 | 7.4 | 29.2 | 99.2 | 16.8 |
| 25 mM Tris, pH 8 | 25 mM Tris, pH 8 | 5.2 | 7.9 | 25 mM Tris, 250 mM NaCl, pH 7.4 | 7.4 | 29.2 | 99.7 | 6.54 |
| 25 mM Tris, pH 8 | 25 mM Tris, pH 8 | 5.2 | 7.9 | 25 mM Tris, 150 mM NaCl, pH 7.4 | 7.5 | 16.72 | 86.5 | 89.4 |
| 25 mM Tris, pH 8 | 25 mM Tris, pH 8 | 5.2 | 7.9 | 25 mM Tris, 150 mM NaCl, pH 7.4 | 7.5 | 16.72 | 88.5 | 88.8 |
| 25 mM Tris, pH 8.5, cond. 6 mS/cm | 25 mM Tris, pH 8.5, cond. 6 mS/cm | 6 | 8.5 | 25 mM Tris, 250 mM NaCl, pH 8 | 8 | 28.5 | 101.3 | 8.62 |
| 25 mM Tris, pH 7.5, cond. 6 mS/cm | 25 mM Tris, pH 7.5, cond. 6 mS/cm | 6 | 7.5 | 25 mM Tris, 250 mM NaCl, pH 7 | 7 | 28.9 | 98.2 | 10.3 |
| 25 mM Tris, pH 7.5, cond. 4 mS/cm | 25 mM Tris, pH 7.5, cond. 4 mS/cm | 4 | 7.5 | 25 mM Tris, 100 mM NaCl, pH 8 | 8 | 13 | 43.8 | 100 |
| 25 mM Tris, pH 8, cond. 5 mS/cm | 25 mM Tris, pH 8, cond. 5 mS/cm | 5 | 8 | 25 mM Tris, 175 mM NaCl, pH 7.5 | 7.5 | 21.6 | 98.2 | 79.3 |
| 25 mM Tris, pH 8, cond. 5 mS/cm | 25 mM Tris, pH 8, cond. 5 mS/cm | 5 | 8 | 25 mM Tris, 175 mM NaCl, pH 7.5 | 7.5 | 21.6 | 95.8 | 78.4 |
| 25 mM Tris, pH 8.5, cond. 6 mS/cm | 25 mM Tris, pH 8.5, cond. 6 mS/cm | 6 | 8.5 | 25 mM Tris, 100 mM NaCl, pH 7 | 7 | 13.9 | 50.5 | 100 |

-continued

Resin: Fractogel ® EMD TMAE HiCap

| Equil. Buffer | Wash Buffer | Load Cond. (mS/cm) | Load pH | Elution Buffer | Elution Buffer pH | Elution Buffer Cond. (mS/cm) | Yield (%) | Leach Prot A Reduct (%) |
|---|---|---|---|---|---|---|---|---|
| 25 mM Tris, pH 8.5, cond. 4 mS/cm | 25 mM Tris, pH 8.5, cond. 4 mS/cm | 4 | 8.5 | 25 mM Tris, 250 mM NaCl, pH 7 | 7 | 13.9 | 100.2 | 6.25 |
| 25 mM Tris, pH 8.5, cond. 6 mS/cm | 25 mM Tris, pH 8.5, cond. 6 mS/cm | 6 | 8.5 | 25 mM Tris, 250 mM NaCl, pH 7 | 7 | 28.9 | 100 | 11.2 |
| 25 mM Tris, pH 8.5, cond. 4 mS/cm | 25 mM Tris, pH 8.5, cond. 4 mS/cm | 4 | 8.5 | 25 mM Tris, 100 mM NaCl, pH 8 | 8 | 13 | 46.2 | 100 |
| 25 mM Tris, pH 8, cond. 5 mS/cm | 25 mM Tris, pH 8, cond. 5 mS/cm | 5 | 8 | 25 mM Tris, 175 mM NaCl, pH 7.5 | 7.5 | 21.6 | 98.1 | 82 |
| 25 mM Tris, pH 7.5, cond. 4 mS/cm | 25 mM Tris, pH 7.5, cond. 4 mS/cm | 4 | 7.5 | 25 mM Tris, 100 mM NaCl, pH 7 | 7 | 13.9 | 56.2 | 100 |
| 25 mM Tris, pH 8, cond. 5 mS/cm | 25 mM Tris, pH 8, cond. 5 mS/cm | 5 | 8 | 25 mM Tris, 175 mM NaCl, pH 7.5 | 7.5 | 21.6 | 96.6 | 81.1 |
| 25 mM Tris, pH 7.5, cond. 6 mS/cm | 25 mM Tris, pH 7.5, cond. 6 mS/cm | 6 | 7.5 | 25 mM Tris, 100 mM NaCl, pH 8 | 8 | 13 | 32.9 | 100 |
| 25 mM Tris, pH 7.5, cond. 4 mS/cm | 25 mM Tris, pH 7.5, cond. 4 mS/cm | 4 | 7.5 | 25 mM Tris, 100 mM NaCl, pH 8 | 8 | 13 | 42.2 | 100 |
| 25 mM Tris, pH 8.5, cond. 6 mS/cm | 25 mM Tris, pH 8.5, cond. 6 mS/cm | 6 | 8.5 | 25 mM Tris, 100 mM NaCl, pH 7 | 7 | 13.9 | 43.9 | 81.9 |
| 25 mM Tris, pH 8, cond. 5 mS/cm | 25 mM Tris, pH 8, cond. 5 mS/cm | 5 | 8 | 25 mM Tris, 175 mM NaCl, pH 7.5 | 7.5 | 21.6 | 97 | 74.8 |
| 25 mM Tris, pH 8, cond. 5 mS/cm | 25 mM Tris, pH 8, cond. 5 mS/cm | 5 | 8 | 25 mM Tris, 175 mM NaCl, pH 7.5 | 7.5 | 21.6 | 96.6 | 82.9 |
| 25 mM Tris, pH 8.5, cond. 4 mS/cm | 25 mM Tris, pH 8.5, cond. 4 mS/cm | 4 | 8.5 | 25 mM Tris, 250 mM NaCl, pH 8 | 8 | 28.5 | 98.5 | 25 |
| 25 mM Tris, pH 7.5, cond. 6 mS/cm | 25 mM Tris, pH 7.5, cond. 6 mS/cm | 6 | 7.5 | 25 mM Tris, 250 mM NaCl, pH 8 | 8 | 28.5 | 95.2 | 25.9 |
| 25 mM Tris, pH 7.5, cond. 4 mS/cm | 25 mM Tris, pH 7.5, cond. 4 mS/cm | 4 | 7.5 | 25 mM Tris, 250 mM NaCl, pH 7 | 7 | 28.9 | 98.9 | 5.77 |
| 25 mM Tris, pH 8.5, cond. 4 mS/cm | 25 mM Tris, pH 8.5, cond. 4 mS/cm | 4 | 8.5 | 25 mM Tris, 100 mM NaCl, pH 7 | 7 | 13.9 | 55.6 | 100 |
| 25 mM Tris, pH 7.5, cond. 6 mS/cm | 25 mM Tris, pH 7.5, cond. 6 mS/cm | 6 | 7.5 | 25 mM Tris, 100 mM NaCl, pH 7 | 7 | 13.9 | 45 | 100 |
| 25 mM Tris, pH 8.5, cond. 6 mS/cm | 25 mM Tris, pH 8.5, cond. 6 mS/cm | 6 | 8.5 | 25 mM Tris, 250 mM NaCl, pH 7 | 7 | 28.9 | 100.3 | 24.1 |
| 25 mM Tris, pH 8, cond. 5 mS/cm | 25 mM Tris, pH 8, cond. 5 mS/cm | 5 | 8 | 25 mM Tris, 175 mM NaCl, pH 7.5 | 7.5 | 21.6 | 97.5 | 84.7 |

-continued

| | | | | | | | | |
|---|---|---|---|---|---|---|---|---|
| | Resin: Fractogel ® EMD TMAE HiCap | | | | | | | |

| Equil. Buffer | Wash Buffer | Load Cond. (mS/cm) | Load pH | Elution Buffer | Elution Buffer pH | Elution Buffer Cond. (mS/cm) | Yield (%) | Leach Prot A Reduct (%) |
|---|---|---|---|---|---|---|---|---|
| 25 mM Tris, pH 8.5, cond. 6 mS/cm | 25 mM Tris, pH 8.5, cond. 6 mS/cm | 6 | 8.5 | 25 mM Tris, 100 mM NaCl, pH 8 | 8 | 13 | 34.3 | 100 |
| 25 mM Tris, pH 7.5, cond. 4 mS/cm | 25 mM Tris, pH 7.5, cond. 4 mS/cm | 4 | 7.5 | 25 mM Tris, 250 mM NaCl, pH 8 | 8 | 28.5 | 98.6 | 11.5 |
| 25 mM Tris, pH 8, cond. 5 mS/cm | 25 mM Tris, pH 8, cond. 5 mS/cm | 5 | 8 | 25 mM Tris, 175 mM NaCl, pH 7.5 | 7.5 | 21.6 | 95.2 | 82 |
| 25 mM Tris, pH 8, cond. 5 mS/cm | 25 mM Tris, pH 8, cond. 5 mS/cm | 5 | 8 | 25 mM Tris, pH 7.2, cond 20 mS/cm | 7.2 | 20 | 91.6 | 70.1 |
| 25 mM Tris, pH 8, cond. 5 mS/cm | 25 mM Tris, pH 8, cond. 5 mS/cm | 5 | 8 | 25 mM Tris, pH 7.2, cond 20 mS/cm | 7.2 | 20 | 90.6 | 85.1 |
| 25 mM Tris, pH 8, cond. 5 mS/cm | 25 mM Tris, pH 8, cond. 5 mS/cm | 5 | 8 | 25 mM Tris, pH 7.2, cond 20 mS/cm | 7.2 | 20 | 94 | 87.4 |
| 25 mM Tris, pH 8, cond. 5 mS/cm | 25 mM Tris, pH 8, cond. 5 mS/cm | 5 | 8 | 25 mM Tris, pH 7.2, cond 20 mS/cm | 7.2 | 20 | 91.4 | 82.9 |
| 25 mM Tris, pH 8, cond. 5 mS/cm | 25 mM Tris, pH 8, cond. 5 mS/cm | 5 | 8 | 25 mM Tris, pH 7.2, cond 20 mS/cm | 7.2 | 20 | 91.7 | 88 |
| 25 mM Tris, pH 8, cond. 5 mS/cm | 25 mM Tris, pH 8, cond. 5 mS/cm | 5 | 8 | 25 mM Tris, pH 7.2, cond 20 mS/cm | 7.2 | 20 | 87.8 | 81.9 |
| 25 mM Tris, pH 8, cond. 5 mS/cm | 25 mM Tris, pH 8, cond. 5 mS/cm | 5 | 8 | 25 mM Tris, pH 7.2, cond 20 mS/cm | 7.2 | 21.2 | 91.7 | 61.4 |
| 25 mM Tris, pH 8, cond. 5 mS/cm | 25 mM Tris, pH 8, cond. 5 mS/cm | 5 | 8 | 25 mM Tris, pH 7.2, cond 20 mS/cm | 7.2 | 20 | 95.7 | 61.7 |
| 25 mM Tris, pH 8, cond. 5 mS/cm | 25 mM Tris, pH 8, cond. 5 mS/cm | 5 | 8 | 25 mM Tris, pH 7.2, cond 20 mS/cm | 7.2 | 20 | 95.7 | 65 |
| 25 mM Tris, pH 8, cond. 5 mS/cm | 25 mM Tris, pH 8, cond. 5 mS/cm | 5 | 8 | 25 mM Tris, pH 7.2, cond 20 mS/cm | 7.2 | 20 | 91.6 | 70 |
| 25 mM Tris, pH 8, cond. 5 mS/cm | 25 mM Tris, pH 8, cond. 5 mS/cm | 5 | 8 | 25 mM Tris, pH 7.2, cond 20 mS/cm | 7.2 | 20 | 94.9 | 65.9 |
| 25 mM Tris, pH 8, cond. 5 mS/cm | 25 mM Tris, pH 8, cond. 5 mS/cm | 5 | 8 | 25 mM Tris, pH 7.2, cond 20 mS/cm | 7.2 | 20 | 92.7 | 68.4 |
| 25 mM Tris, pH 8, cond. 5 mS/cm | 25 mM Tris, pH 8, cond. 5 mS/cm | 5 | 8 | 25 mM Tris, pH 7.2, cond 20 mS/cm | 7.2 | 20 | 97.9 | 86.2 |
| 25 mM Tris, pH 8, cond. 5 mS/cm | 25 mM Tris, pH 8, cond. 5 mS/cm | 5 | 8 | 25 mM Tris, pH 7.2, cond 20 mS/cm | 7.2 | 20 | 97.4 | 61.1 |
| 25 mM Tris, | 25 mM Tris, pH | 5 | 8 | 25 mM Tris, 180 mM NaCl, | 7.2 | 19.6 | 96 | 69.6 |

Resin: Fractogel ® EMD TMAE HiCap

| Equil. Buffer | Wash Buffer | Load Cond. (mS/cm) | Load pH | Elution Buffer | Elution Buffer pH | Elution Buffer Cond. (mS/cm) | Yield (%) | Leach Prot A Reduct (%) |
|---|---|---|---|---|---|---|---|---|
| 33 mM NaCl, pH 8, cond. 5 mS/cm | 8, cond. 5 mS/cm | | | pH 7.2 | | | | |
| 25 mM Tris, 33 mM NaCl, pH 8, cond. 5 mS/cm | 25 mM Tris, pH 8, cond. 5 mS/cm | 5 | 8 | 25 mM Tris, 180 mM NaCl, pH 7.2 | 7.2 | 19.6 | 96.3 | 72 |
| 25 mM Tris, 33 mM NaCl, pH 8, cond. 5 mS/cm | 25 mM Tris, pH 8, cond. 5 mS/cm | 5 | 8 | 25 mM Tris, 160 mM NaCl, pH 7.2 | 7.2 | 20 | 92.7 | 67.8 |
| 25 mM Tris, pH 8 | 25 mM Tris, 45 mM NaCl, pH 8.0 | 4.61 | 7.91 | 25 mM Tris, 150 mM NaCl, pH 7.4 | 7.4 | not recorded | 82.3 | 93.9 |
| 25 mM Tris, pH 8 | 25 mM Tris, 45 mM NaCl, pH 8.0 | 4.58 | 7.87 | 25 mM Tris, 150 mM NaCl, pH 7.4 | 7.4 | not recorded | 82.7 | 94.3 |
| 25 mM Tris, pH 8 | 25 mM Tris, 45 mM NaCl, pH 8.0 | 4.75 | 7.87 | 25 mM Tris, 150 mM NaCl, pH 7.4 | 7.4 | not recorded | not recorded | 92 |

Figure 2:
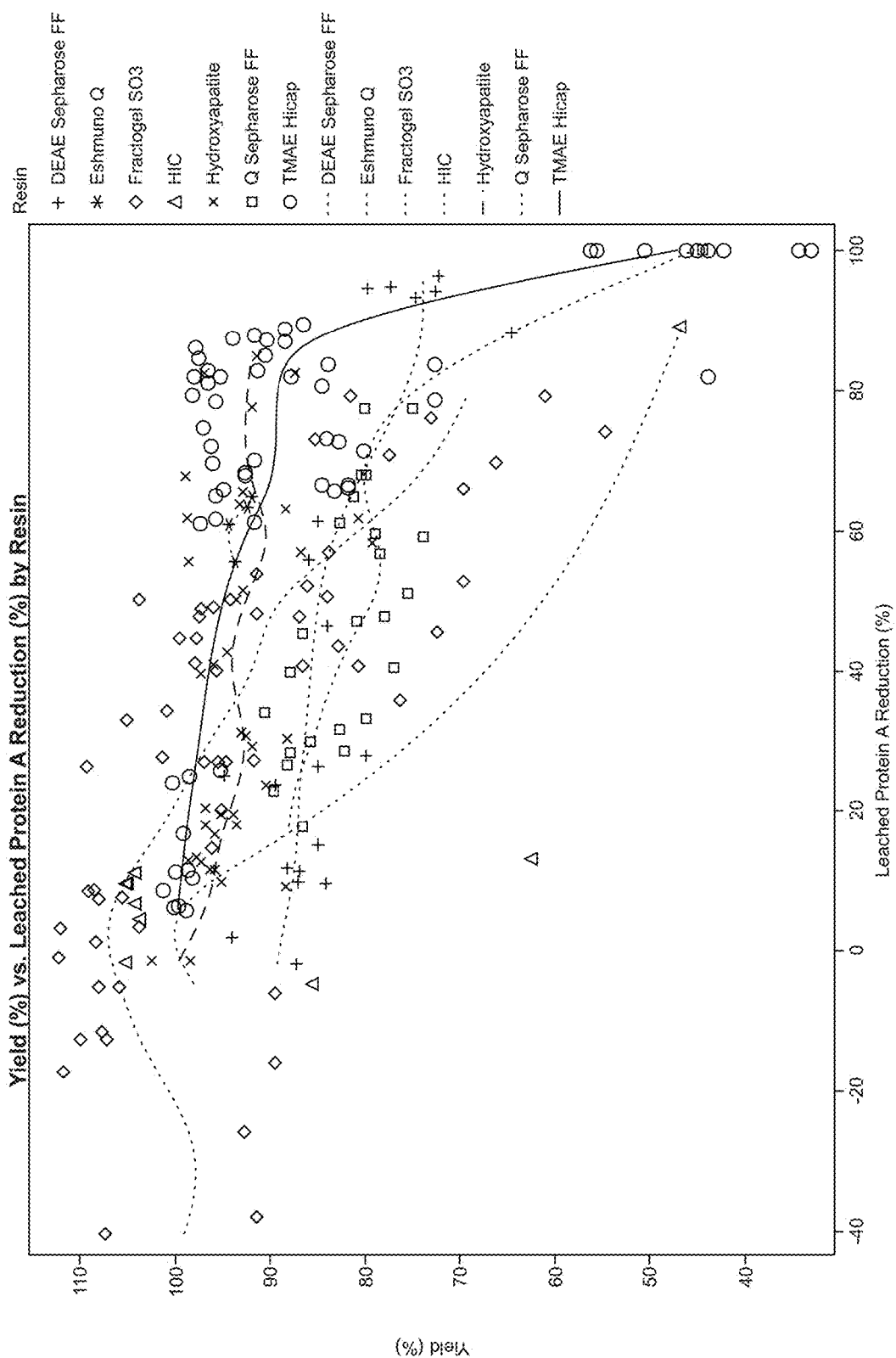
FIG. 2 is an overlay of the Recovery/Leached Protein A Reduction curves graphed in FIG. 1. Symbols used in the graph for each resin are indicated in the figure legend.

As compared to the other anion, cation, and hydrophobic interaction chromatography resins analyzed, Fractogel® EMD TMAE HiCap was surprisingly good at removing Protein A while allowing for a very high recovery of the target protein. The results from all of the resins that were thoroughly investigated were graphed in FIG. 1. An overlay of all of the resins into one overall scatterplot is shown in FIG. 2. The general trend for all resins is of decreasing yield with increasing protein A removal. However, in the fully optimized portion of the data, there is a "shoulder" that contains only results using either Hydroxyapaptite or Fractogel® EMD TMAE HiCap resins.

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method for purifying an antibody from a sample containing the antibody and a second protein that binds to the antibody, comprising subjecting the sample to a tentacle anion exchange matrix chromatography medium under conditions whereby the antibody binds to the tentacle anion exchange matrix chromatography medium, followed by eluting the antibody bound to the chromatography medium in an eluant, whereby at least 85% of the antibody is recovered in the eluant and at least 75% of the second protein is removed from the eluant, wherein the second protein is Protein A or Protein G.

2. The method of claim 1, wherein the antibody is a humanized antibody or human antibody.

3. The method of claim 1, wherein the antibody is adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, zalutumumab, or zanolimumab.

4. The method of claim 1, wherein the antibody is denosumab.

5. The method of claim 1, wherein the tentacle anion exchange matrix chromatography medium contains a strong anion functional group.

6. The method of claim 5, wherein the strong anion functional group is trimethyl-ammoniumethyl (TMAE).

7. The method of claim 1, wherein the tentacle anion exchange matrix chromatography medium is a methacrylate polymeric resin or a polyvinylstyrene polymeric resin.

8. The method of claim 1, wherein the chromatography medium is a methacrylate polymeric resin.

9. The method of claim 1, wherein the sample is obtained from affinity purification of the antibody over a Protein A chromatography medium.

10. The method of claim 1, wherein the sample is subjected to the tentacle anion exchange matrix chromatography medium at about pH 8.

11. The method of claim 1, wherein after the antibody is bound to the tentacle anion exchange matrix chromatography medium and before the antibody is eluted, the tentacle anion exchange matrix chromatography medium is subjected to a wash step.

12. The method of claim 11, wherein the wash step comprises washing the tentacle anion exchange matrix chromatography medium with a buffered solution at about pH 8.

13. The method of claim 12, wherein the buffered solution consists essentially of 25 mM Tris(hydroxymethyl)aminomethane (Tris) at about pH 8.

14. The method of claim 1, wherein the antibody is eluted from the tentacle anion exchange matrix chromatography medium in an elution buffer at a pH of from about 7.2 to about 7.5.

15. The method of claim 14, wherein the elution buffer is 25 mM Tris HCl, pH 7.2.

16. The method of claim 14, wherein the elution buffer is 25 mM Tris HCl, pH 7.5 and NaCl from about 150 mM to about 200 mM.

17. The method of claim 1, wherein the antibody is subjected to a further purification step before or after the tentacle anion exchange matrix chromatography.

18. The method of claim 17, wherein the antibody is formulated in a pharmaceutical composition after the purification.

19. A method for purifying an antibody from a sample containing the antibody and a second protein that binds to the antibody, comprising subjecting the sample to a tentacle anion exchange matrix chromatography medium in a buffer at about pH 8, followed by eluting the antibody bound to the chromatography medium in an eluant, wherein the second protein is Protein A or Protein G.

20. The method of claim 19, wherein the antibody is adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, zalutumumab, or zanolimumab.

21. The method of claim 20, wherein the antibody is denosumab.

22. The method of claim 19, wherein the resin substrate of the tentacle anion exchange matrix chromatography medium is a methacrylate polymeric resin or a polyvinylstyrene polymeric resin.

23. The method of claim 19, wherein the sample is obtained from affinity purification of the antibody over a Protein A chromatography medium.

24. The method of claim 19, wherein after the antibody is bound to the tentacle anion exchange matrix chromatography medium and before the antibody is eluted, the tentacle anion exchange matrix chromatography medium is subjected to a wash step.

25. The method of claim 24, wherein the wash step comprises washing the tentacle anion exchange matrix chromatography medium with a buffered solution at about pH 8.

26. The method of claim 19, wherein the antibody is eluted from the tentacle anion exchange matrix chromatography medium in an elution buffer at a pH of from 7.2 to 7.6.

27. The method of claim 26, wherein the elution buffer is 25 mM Tris HCl, pH 7.2; or wherein the elution buffer is 25 mM Tris HCl, pH 7.5 and NaCl from 150 mM to 200 mM.

28. The method of claim 19, wherein the tentacle anion exchange matrix chromatography medium contains TMAE, and wherein the buffer is a Tris buffer.

* * * * *